US012790636B2

(12) United States Patent
Knopfmacher et al.

(10) Patent No.: US 12,790,636 B2
(45) Date of Patent: Nov. 10, 2026

(54) APPARATUS, SYSTEMS, AND METHODS FOR DETERMINING THE SUSCEPTIBILITY OF INFECTIOUS AGENTS TO ANTI-INFECTIVES

(71) Applicant: Avails Medical, Inc., Menlo Park, CA (US)

(72) Inventors: Oren S. Knopfmacher, San Francisco, CA (US); Meike Herget, Woodside, CA (US); Nitin K. Rajan, Palo Alto, CA (US); Ashraf M. Wahba, Hayward, CA (US)

(73) Assignee: Avails Medical, Inc., Menlo Park, CA (US)

( * ) Notice: Subject to any disclaimer, the term of this patent is extended or adjusted under 35 U.S.C. 154(b) by 210 days.

(21) Appl. No.: 18/896,619

(22) Filed: Sep. 25, 2024

(65) Prior Publication Data

US 2025/0011830 A1 Jan. 9, 2025

Related U.S. Application Data

(63) Continuation of application No. 17/241,991, filed on Apr. 27, 2021, now Pat. No. 12,129,509, and a continuation of application No. PCT/US2019/058043, filed on Oct. 25, 2019.

(60) Provisional application No. 62/752,982, filed on Oct. 30, 2018.

(51) Int. Cl.

| | |
|---|---|
| ***C12Q 1/18*** | (2006.01) |
| ***G01N 27/30*** | (2006.01) |
| ***G01N 27/327*** | (2006.01) |

(52) U.S. Cl.
CPC .......... *C12Q 1/18* (2013.01); *G01N 27/3275* (2013.01); *G01N 27/302* (2013.01)

(58) Field of Classification Search
None
See application file for complete search history.

(56) References Cited

U.S. PATENT DOCUMENTS

| | | | |
|---|---|---|---|
| 4,209,586 | A | 6/1980 | Noller |
| 2004/0195098 | A1 | 10/2004 | Broadley et al. |
| 2013/0217063 | A1 | 8/2013 | Metzger et al. |
| 2016/0068417 | A1 | 3/2016 | Buschmann |
| 2017/0059508 | A1 | 3/2017 | Knopfmacher et al. |

(Continued)

FOREIGN PATENT DOCUMENTS

| | | |
|---|---|---|
| WO | WO 2020/092148 | 5/2020 |

*Primary Examiner* — J. Christopher Ball
(74) *Attorney, Agent, or Firm* — Levine Bagade Han LLP

(57) ABSTRACT

Various methods, devices, and systems for determining the susceptibility of infectious agents to anti-infectives are disclosed herein. A method comprises introducing an inoculum solution comprising the infectious agent into a sample receiving space of a diagnostic device. The sample receiving space comprises a plurality of growth control wells devoid of the anti-infective and a plurality of active electrode wells comprising the anti-infective at differing concentrations. A water immiscible liquid can be introduced into the sample receiving space to seal the plurality of wells and the diagnostic device can be incubated for a period of time. The minimum inhibitory concentration (MIC) of the anti-infective on the infectious agent can be determined by monitoring and comparing one or more solution characteristics of the inoculum solution within the active electrode wells with the one or more solution characteristics of the inoculum solution with the growth control wells.

20 Claims, 7 Drawing Sheets

(56) References Cited

U.S. PATENT DOCUMENTS

| | | | |
|---|---|---|---|
| 2018/0195106 | A1 | 7/2018 | Knopfmacher et al. |
| 2021/0262003 | A1 | 8/2021 | Knopfmacher et al. |

GROWTH CURVE OF *E. COLI* IN THE PRESENCE OF DIFFERING CONCENTRATIONS OF LEVOFLOXACIN (LVX)

GROWTH CURVE OF *E. COLI* IN THE PRESENCE OF DIFFERING CONCENTRATIONS OF CIPROFLOXACIN (CIP)

GROWTH CURVE OF *E. COLI* IN THE PRESENCE OF DIFFERING CONCENTRATIONS OF CIPROFLOXACIN (CIP)

APPARATUS, SYSTEMS, AND METHODS FOR DETERMINING THE SUSCEPTIBILITY OF INFECTIOUS AGENTS TO ANTI-INFECTIVES

CROSS-REFERENCE TO RELATED APPLICATIONS

This application is a continuation of U.S. patent application Ser. No. 17/241,991 filed on Apr. 27, 2021, which is a continuation of PCT Application No. PCT/US2019/058043 filed on Oct. 25, 2019, which claims the benefit of U.S. Provisional Application No. 62/752,982 filed on Oct. 30, 2018, the contents of which are incorporated herein by reference in their entireties.

TECHNICAL FIELD

The present disclosure relates generally to in vitro diagnostic testing of infectious agents and, more specifically, to apparatus, systems, and methods for determining the susceptibility of such infectious agents to anti-infectives.

BACKGROUND

Infections caused by anti-infective resistant microorganisms or infectious agents are a significant problem for healthcare professionals in hospitals, nursing homes, and other healthcare environments. Rapid detection of such microorganisms is crucial in order to prevent the spread of their resistance profiles. When faced with such an infection, a preferred course of action is for a clinician to use anti-infective compounds judiciously, preferably only those necessary to alleviate the infection. However, what occurs most frequently today is that broad spectrum anti-infectives are given to the patient to ensure adequacy of treatment. This tends to result in microorganisms with multiple anti-infective resistances. Ideally, the sensitivity of the microorganism to anti-infectives would be detected soon after its presence is identified.

Existing methods and instruments used to detect anti-infective resistance in microorganisms include costly and labor intensive microbial culturing techniques to isolate the microorganism and include tests such as agar disk diffusion or broth microdilution where anti-infectives are introduced as liquid suspensions, paper disks, or dried gradients on agar media. However, those methods require manual interpretation by skilled personnel and are prone to technical or clinician error.

While automated inspection of such panels or media can reduce the likelihood of clinician error, current instruments used to conduct these inspections are often complex and require the addition of reporter molecules or use of costly components such as transparent indium tin oxide (ITO) electrodes. In addition, current instruments often rely on an optical read-out of the investigated samples, which require bulky detection equipment.

As a result of the above limitations and restrictions, there is a need for improved apparatus, systems, and methods to quickly and effectively determine the susceptibility of infectious agents to anti-infectives.

SUMMARY

Disclosed are apparatus, systems, and methods for determining the susceptibility of infectious agents to anti-infectives. In one embodiment, a method of determining a susceptibility of an infectious agent to an anti-infective is disclosed. The method comprises introducing an inoculum solution comprising the infectious agent into a sample receiving space of a diagnostic device through a sample inlet port. The sample receiving space can comprise a plurality of wells comprising a plurality of pH electrode wells and a plurality of oxidation reduction potential (ORP) electrode wells. Each of the pH electrode wells can comprise a pH electrode and each of the ORP electrode wells can comprise an ORP electrode. At least one of the pH electrode wells and at least one of the ORP electrode wells are growth control wells devoid of the anti-infective. At least two of the pH electrode wells and at least two of the ORP electrode wells are active electrode wells comprising the anti-infective at differing concentrations. The method als comprises introducing a reference buffer into a buffer receiving space of the diagnostic device through a buffer inlet port. In some embodiments, the reference buffer can be a reference buffer gel.

The buffer receiving space can comprise a plurality of reference electrode wells. Each of the reference electrode wells can comprise a reference electrode. In some embodiments, the reference electrodes can comprise platinum, gold, stainless steel, or a combination thereof.

Each of the reference electrode wells can be in fluid communication with one of the pH electrode wells and one of the ORP electrode wells. The reference electrode wells can be connected to the pH electrode wells and the ORP electrode wells via a plurality of connecting conduits.

The method can further comprise introducing a water immiscible liquid into the sample receiving space through the sample inlet port and incubating the diagnostic device comprising the inoculum solution and the water immiscible liquid for a predetermined time period. In some embodiments, the water immiscible liquid can be a silicone oil, a non-polar solvent, or a combination thereof.

The method can also comprise monitoring one or more solution characteristics of the inoculum solution within the active electrode wells and the growth control wells over the predetermined time period and comparing the one or more solution characteristics of the inoculum solution within the growth control wells with the one or more solution characteristics of the inoculum solution within the active electrode wells to determine the minimum inhibitory concentration (MIC) of the anti-infective on the infectious agent.

Disclosed is also a system to determine a susceptibility of an infectious agent to an anti-infective. The system can comprise a diagnostic device comprising a sample receiving space. The sample receiving space can be configured to receive an inoculum solution through a sample inlet port of the diagnostic device. The sample receiving space can comprise a plurality of wells comprising a plurality of pH electrode wells and a plurality of oxidation reduction potential (ORP) electrode wells. Each of the pH electrode wells can comprise a pH electrode and each of the ORP electrode wells can comprise an ORP electrode. At least one of the pH electrode wells and at least one of the ORP electrode wells can be growth control wells devoid of the anti-infective. At least two of the pH electrode wells and at least two of the ORP electrode wells can be active electrode wells comprising the anti-infective at differing concentrations.

The system can also comprise a buffer receiving space The buffer receiving space can be configured to receive a reference buffer through a buffer inlet port of the diagnostic device. The buffer receiving space can comprise a plurality of reference electrode wells. Each of the reference electrode wells can comprise a reference electrode. Each of the reference electrode wells can be in fluid communication with one of the pH electrode wells and one of the ORP electrode wells.

The sample receiving space can be configured to receive a water immiscible liquid through the sample inlet port after the inoculum solution fills the wells of the diagnostic device.

The system can also comprise a parameter analyzer coupled to the diagnostic device The parameter analyzer can be configured to monitor one or more solution characteristics of the inoculum solution within the active electrode wells and the growth control wells over a predetermined time period.

The system can further comprise a computing device coupled to the parameter analyzer. The computing device can be configured to compare the one or more solution characteristics of the inoculum solution within the growth control wells with the one or more solution characteristics of the inoculum solution within the active electrode wells to determine the minimum inhibitory concentration (MIC) of the anti-infective on the infectious agent.

The diagnostic device can comprise a sample outlet port. The inoculum solution can flow into the sample receiving space through the sample inlet port and flows out of the sample receiving space through the sample outlet port. The inoculum solution can flow over the plurality of pH electrode wells and the plurality of ORP electrode wells and fill the pH electrode wells and the ORP electrode wells prior to flowing out of the sample receiving space.

In some embodiments, one of the solution characteristics of the inoculum solution is pH and the MIC of the anti-infective on the infectious agent is determined by comparing the pH of the inoculum solution within the growth control well comprising the pH electrode with the pH of the inoculum solution within the active electrode wells comprising the pH electrodes. In other embodiments, one of the solution characteristics of the inoculum solution is ORP and the MIC of the anti-infective on the infectious agent is determined by comparing the ORP of the inoculum solution within the growth control well comprising the ORP electrode with the ORP of the inoculum solution within the active electrode wells comprising the ORP electrodes. In further embodiments, the solution characteristics of the inoculum solution are pH and ORP and the MIC of the anti-infective on the infectious agent is determined by comparing the pH and the ORP of the inoculum solution within the growth control wells with the pH and the ORP of the inoculum solution within the active electrode wells.

The active electrode wells can comprise at least a first pH electrode well, a second pH electrode well, a first ORP electrode well, and a second ORP electrode well. The first pH electrode well and the first ORP electrode well can comprise the anti-infective at a first concentration. The second pH electrode well and the second ORP electrode well can comprise the anti-infective at a second concentration. The first concentration of the anti-infective can be double the second concentration.

The active electrode wells can comprise the anti-infective in at least one of a dried form and a lyophilized form. In some embodiments, the active electrode wells and the growth control wells can comprise a nutrient solution in dried form. Each of the wells can have a well diameter and a well depth. An aspect ratio of the well depth to the well diameter can be between about 1:1 to about 1:2.

Each of the ORP electrodes can comprise a redox sensitive material. The redox sensitive material can comprise at least one of silicon dioxide ($SiO_2$), aluminum oxide ($Al_2O_3$), titanium dioxide ($TiO_2$), tantalum pentoxide ($Ta_2O_5$), hafnium dioxide ($HfO_2$), iridium dioxide ($IrO_2$), ruthenium dioxide ($RuO_2$), zirconium dioxide ($ZrO_2$), or a combination thereof.

Each of the pH electrodes can comprise a pH sensitive material. The pH sensitive material can comprise at least one of silicon dioxide ($SiO_2$), aluminum oxide ($Al_2O_3$), titanium dioxide ($TiO_2$), tantalum pentoxide ($Ta_2O_5$), hafnium dioxide ($HfO_2$), or a combination thereof.

Also disclosed is another method of determining a susceptibility of an infectious agent to an anti-infective. The method can comprise introducing an inoculum solution comprising the infectious agent into a sample receiving space of a diagnostic device through a sample inlet port. The sample receiving space can comprise a plurality of wells. Each of the plurality of wells can comprise a pH electrode, an oxidation reduction potential (ORP) electrode, and a reference electrode. At least one of the wells can be a growth control well devoid of the anti-infective. At least two of the remaining wells can be active electrode wells comprising the anti-infective at differing concentrations.

The method can also comprise introducing a water immiscible liquid into the sample receiving space through the sample inlet port and incubating the diagnostic device comprising the inoculum solution and the water immiscible liquid for a predetermined time period. The water immiscible liquid can be a silicone oil, a non-polar solvent, or a combination thereof.

The method can further comprise monitoring one or more solution characteristics of the inoculum solution within the active electrode wells and the growth control well over the predetermined time period and comparing the one or more solution characteristics of the inoculum solution within the growth control well with the one or more solution characteristics of the inoculum solution within the active electrode wells to determine the minimum inhibitory concentration (MIC) of the anti-infective on the infectious agent.

Also disclosed is a system to determine a susceptibility of an infectious agent to an anti-infective. The system can comprise a diagnostic device comprising a sample receiving space. The sample receiving space can be configured to receive an inoculum solution through a sample inlet port of the diagnostic device. The sample receiving space can comprise a plurality of wells. Each of the plurality of wells can comprise a pH electrode, an oxidation reduction potential (ORP) electrode, and a reference electrode.

The ORP electrode can comprise a redox sensitive material. The redox sensitive material can comprise at least one of silicon dioxide ($SiO_2$), aluminum oxide ($Al_2O_3$), titanium dioxide ($TiO_2$), tantalum pentoxide ($Ta_2O_5$), hafnium dioxide ($HfO_2$), iridium dioxide ($IrO_2$), ruthenium dioxide ($RuO_2$), and zirconium dioxide ($ZrO_2$).

The pH electrode can comprise a pH sensitive material. The pH sensitive material can comprise at least one of silicon dioxide ($SiO_2$), aluminum oxide ($Al_2O_3$), titanium dioxide ($TiO_2$), tantalum pentoxide ($Ta_2O_5$), and hafnium dioxide ($HfO_2$). The reference electrode can comprise platinum, gold, stainless steel, or a combination thereof.

At least one of the wells can be a growth control well devoid of the anti-infective. At least two of the remaining wells can be active electrode wells comprising the anti-infective at differing concentrations. The sample receiving space can be configured to receive a water immiscible liquid through the sample inlet port after the inoculum solution fills the wells of the diagnostic device.

The diagnostic device can comprise a sample outlet port. The inoculum solution can flow into the sample receiving space through the sample inlet port and flow out of the sample receiving space through the sample outlet port. The inoculum solution can flow over the wells and fill the wells prior to flowing out of the sample receiving space.

The system can further comprise a parameter analyzer coupled to the diagnostic device. The parameter analyzer can be configured to monitor one or more solution characteristics of the inoculum solution within the active electrode wells and the growth control well over a predetermined time period.

The system can also comprise a computing device coupled to the parameter analyzer. The computing device can be configured to compare the one or more solution characteristics of the inoculum solution within the growth control well with the one or more solution characteristics of the inoculum solution within the active electrode wells to determine the minimum inhibitory concentration (MIC) of the anti-infective on the infectious agent.

In some embodiments, one of the solution characteristics monitored can be pH and the MIC of the anti-infective on the infectious agent can be determined by comparing the pH of the inoculum solution within the growth control well with the pH of the inoculum solution within the active electrode wells. In these and other embodiments, one of the solution characteristics monitored can be ORP and the MIC of the anti-infective on the infectious agent can be determined by comparing the ORP of the inoculum solution within the growth control well with the ORP of the inoculum solution within the active electrode wells. In addition embodiments, the solution characteristics monitored can be pH and ORP and the MIC of the anti-infective on the infectious agent can be determined by comparing the pH and the ORP of the inoculum solution within the growth control well with the pH and the ORP of the inoculum solution within the active electrode wells.

The active electrode wells can comprise at least a first well and a second well. The first well can comprise the anti-infective at a first concentration. The second well can comprise the anti-infective at a second concentration. The first concentration of the anti-infective can be double the second concentration.

The active electrode wells can comprise the anti-infective in at least one of a dried form and a lyophilized form. The active electrode wells and the growth control wells can comprise a nutrient solution in dried form.

Each of the wells can have a well diameter and a well depth. An aspect ratio of the well depth to the well diameter can be between about 1:1 to about 1:2.

DETAILED DESCRIPTION

Variations of the devices, systems, and methods described herein are best understood from the detailed description when read in conjunction with the accompanying drawings. It is emphasized that, according to common practice, the various features of the drawings may not be to scale. On the contrary, the dimensions of the various features may be arbitrarily expanded or reduced for clarity and not all features may be visible or labeled in every drawing. The drawings are taken for illustrative purposes only and are not intended to define or limit the scope of the claims to that which is shown.

Figure 1:
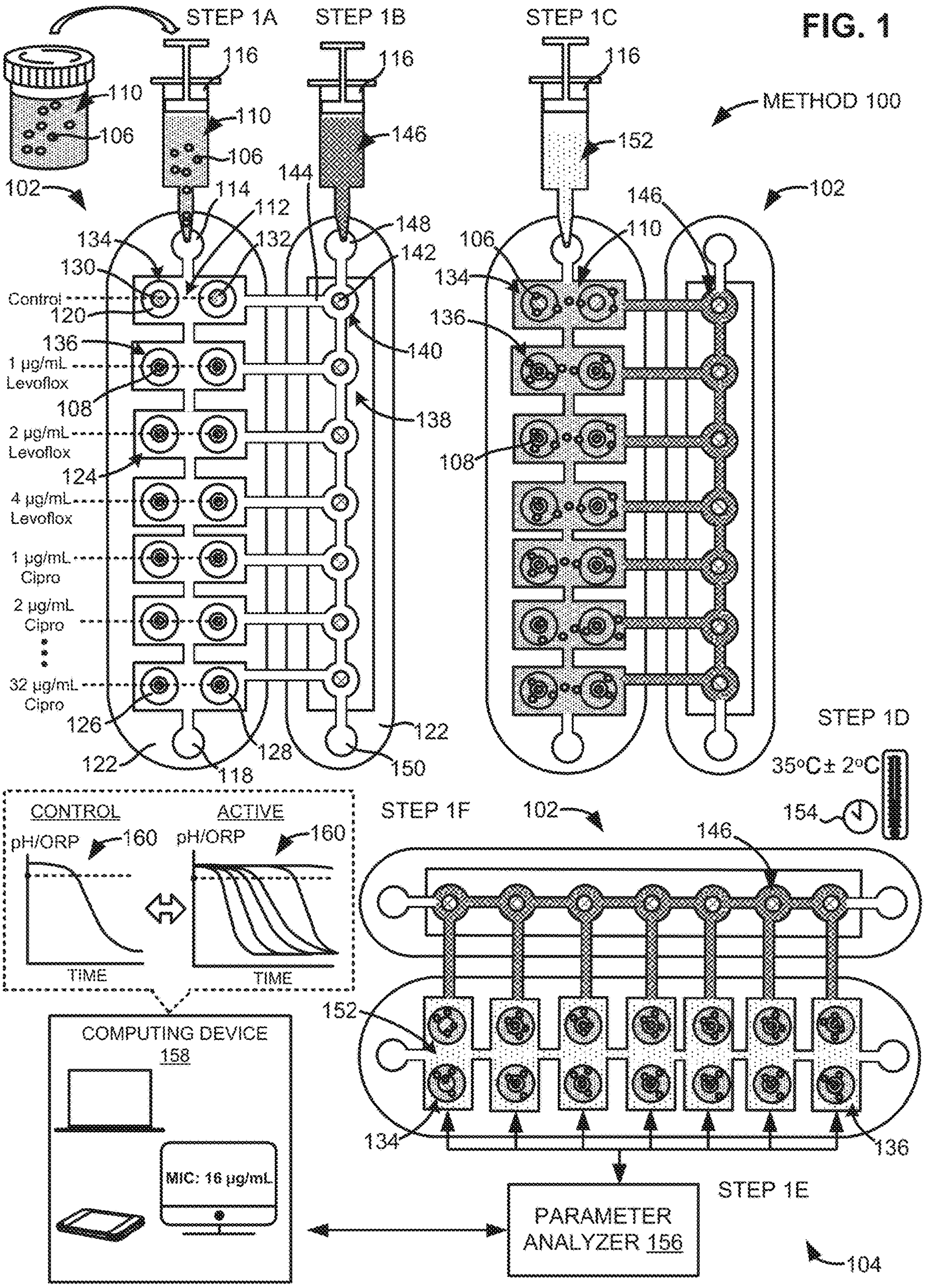
FIG. 1 illustrates embodiments of a method, diagnostic device, and system for determining the susceptibility of an infectious agent to an anti-infective.

FIG. 1 illustrates embodiments of a method 100, a diagnostic device 102, and a system 104 for determining a susceptibility of an infectious agent 106 to an anti-infective 108.

The method 100 can comprise introducing an inoculum solution 110 comprising the infectious agent 106 into a sample receiving space 112 of the diagnostic device 102 through a sample inlet port 114 of the diagnostic device 102 in step 1A. The sample inlet port 114 can be an opening or conduit in fluid communication with the sample receiving space 112.

The inoculum solution 110 can be prepared from or comprise at least one of a biological sample, a bodily fluid, a wound swab or sample, a rectal swab or sample, and a bacterial culture derived from the biological sample, the bodily fluid, the wound swab or sample, or the rectal swab or sample. The bodily fluid can comprise urine, blood, serum, plasma, saliva, sputum, semen, breast milk, joint fluid, spinal fluid, wound material, mucus, fluid accompanying stool, re-suspended rectal or wound swabs, vaginal secretions, cerebrospinal fluid, synovial fluid, pleural fluid, peritoneal fluid, pericardial fluid, amniotic fluid, cultures of bodily which has been tested positive for the infectious agent 106 such as blood culture which has been tested positive for bacteria or bacterial growth (i.e., a positive blood culture), or a combination thereof.

Infectious agents 106 that can be assayed for anti-infective susceptibility using the methods or systems disclosed herein can be any metabolizing single- or multi-cellular organism including bacteria and fungi. In certain embodiments, the infectious agent 106 can be bacteria selected from the genera *Acinetobacter, Acetobacter, Actinomyces, Aerococcus, Aeromonas, Agrobacterium, Anaplasma, Azorhizobium, Azotobacter, Bacillus, Bacteriodes, Bartonella, Bordetella, Borrelia, Brucella, Burkholderia, Calymmatobacterium, Campylobacter, Chlamydia, Chlamydophila, Citrobacter, Clostridium, Corynebacterium,*

*Coxiella, Ehrlichia, Enterobacter, Enterococcus, Escherichia, Francisella, Fusobacterium, Gardnerella, Haemophilus, Helicobacter, Klebsiella, Lactobacillus, Legionella, Listeria, Methanobacterium, Microbacterium, Micrococcus, Morganella, Moraxella, Mycobacterium, Mycoplasma, Neisseria, Pandoraca, Pasteurella, Peptostreptococcus, Porphyromonas, Prevotella, Proteus, Providencia, Pseudomonas, Ralstonia, Raoultella, Rhizobium, Rickettsia, Rochalimaca, Rothia, Salmonella, Serratia, Shewanella, Shigella, Spirillum, Staphylococcus, Strenotrophomonas, Streptococcus, Streptomyces, Treponema, Vibrio, Wolbachia, Yersinia*, or a combination thereof. In other embodiments, the infectious agent 106 can be one or more fungi selected from the genera *Candida* or *Cryptococcus* or mold.

Other specific bacteria that can be assayed for anti-infective susceptibility using the methods and systems disclosed herein can comprise *Staphylococcus aureus, Staphylococcus lugdunensis*, coagulase-negative *Staphylococcus* species (including but not limited to *Staphylococcus epidermidis, Staphylococcus haemolyticus, Staphylococcus hominis, Staphylococcus capitis*, not differentiated), *Enterococcus faecalis, Enterococcus faecium* (including but not limited to *Enterococcus faecium* and other *Enterococcus* spp., not differentiated, excluding *Enterococcus faecalis*), *Streptococcus pneumoniae, Streptococcus pyogenes, Streptococcus agalactiae, Streptococcus* spp., (including but not limited to *Streptococcus mitis, Streptococcus pyogenes, Streptococcus gallolyticus, Streptococcus agalactiae, Streptococcus pneumoniae*, not differentiated), *Pseudomonas aeruginosa, Acinetobacter baumannii, Klebsiella* spp. (including but not limited to *Klebsiella pneumoniae, Klebsiella oxytoca*, not differentiated), *Escherichia coli, Enterobacter* spp. (including but not limited to *Enterobacter cloacae, Enterobacter aerogenes*, not differentiated), *Proteus* spp. (including but not limited to *Proteus mirabilis, Proteus vulgaris*, not differentiated), *Citrobacter* spp. (including but not limited to *Citrobacter freundii, Citrobacter koseri*, not differentiated), *Serratia marcescens, Candida albicans*, and *Candida glabrata.*

Other more specific bacteria that can be assayed for anti-infective susceptibility can comprise *Acinetobacter baumannii, Actinobacillus* spp., *Actinomycetes, Actinomyces* spp. (including but not limited to *Actinomyces israelii* and *Actinomyces naeslundii*), *Aeromonas* spp. (including but not limited to *Aeromonas hydrophila, Aeromonas veronii* biovar *sobria* (*Aeromonas sobria*), and *Aeromonas caviae*), *Anaplasma phagocytophilum, Alcaligenes xylosoxidans, Actinobacillus actinomycetemcomitans, Bacillus* spp. (including but not limited to *Bacillus anthracis, Bacillus cereus, Bacillus subtilis, Bacillus thuringiensis*, and *Bacillus stearothermophilus*), *Bacteroides* spp. (including but not limited to *Bacteroides fragilis*), *Bartonella* spp. (including but not limited to *Bartonella bacilliformis* and *Bartonella henselae, Bifidobacterium* spp., *Bordetella* spp. (including but not limited to *Bordetella pertussis, Bordetella parapertussis*, and *Bordetella bronchiseptica*), *Borrelia* spp. (including but not limited to *Borrelia recurrentis*, and *Borrelia burgdorferi*), *Brucella* sp. (including but not limited to *Brucella abortus, Brucella canis, Brucella melintensis* and *Brucella suis*), *Burkholderia* spp. (including but not limited to *Burkholderia pseudomallei* and *Burkholderia cepacia*), *Campylobacter* spp. (including but not limited to *Campylobacter jejuni, Campylobacter coli, Campylobacter lari* and *Campylobacter fetus*), *Capnocytophaga* spp., *Cardiobacterium hominis, Chlamydia trachomatis, Chlamydophila pneumoniae, Chlamydophila psittaci, Citrobacter* spp. *Coxiella burnetii, Corynebacterium* spp. (including but not limited to, *Corynebacterium diphtheriae, Corynebacterium jeikeum* and *Corynebacterium*), *Clostridium* spp. (including but not limited to *Clostridium perfringens, Clostridium difficile, Clostridium botulinum* and *Clostridium tetani*), *Eikenella corrodens, Enterobacter* spp. (including but not limited to *Enterobacter aerogenes, Enterobacter agglomerans, Enterobacter cloaca* and *Escherichia coli*, including opportunistic *Escherichia coli*, including but not limited to enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* spp. (including but not limited to *Enterococcus faecalis* and *Enterococcus faecium*) *Ehrlichia* spp. (including but not limited to *Ehrlichia chafeensia* and *Ehrlichia canis*), *Erysipelothrix rhusiopathiae, Eubacterium* spp., *Francisella tularensis, Fusobacterium nucleatum, Gardnerella vaginalis, Gemella morbillorum, Haemophilus* spp. (including but not limited to *Haemophilus influenzae, Haemophilus ducreyi, Haemophilus aegyptius, Haemophilus parainfluenzae, Haemophilus haemolyticus* and *Haemophilus parahaemolyticus, Helicobacter* spp. (including but not limited to *Helicobacter pylori, Helicobacter cinaedi* and *Helicobacter fennelliae*), *Kingella kingii, Klebsiella* spp. (including but not limited to *Klebsiella pneumoniae, Klebsiella granulomatis* and *Klebsiella oxytoca*), *Lactobacillus* spp., *Listeria monocytogenes, Leptospira interrogans, Legionella pneumophila, Leptospira interrogans, Peptostreptococcus* spp., *Moraxella catarrhalis, Morganella* spp., *Mobiluncus* spp., *Micrococcus* spp., *Mycobacterium* spp. (including but not limited to *Mycobacterium leprae, Mycobacterium tuberculosis, Mycobacterium intracellulare, Mycobacterium avium, Mycobacterium bovis*, and *Mycobacterium marinum*), *Mycoplasm* spp. (including but not limited to *Mycoplasma pneumoniae, Mycoplasma hominis*, and *Mycoplasma genitalium*), *Nocardia* spp. (including but not limited to *Nocardia asteroides, Nocardia cyriacigeorgica* and *Nocardia brasiliensis*), *Neisseria* spp. (including but not limited to *Neisseria gonorrhoeae* and *Neisseria meningitidis*), *Pasteurella multocida, Plesiomonas shigelloides, Prevotella* spp., *Porphyromonas* spp., *Prevotella melaninogenica, Proteus* spp. (including but not limited to *Proteus vulgaris* and *Proteus mirabilis*), *Providencia* spp. (including but not limited to *Providencia alcalifaciens, Providencia rettgeri* and *Providencia stuartii*), *Pseudomonas aeruginosa, Propionibacterium acnes, Rhodococcus equi, Rickettsia* spp. (including but not limited to *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* spp., *Serratia marcescens, Stenotrophomonas maltophilia, Salmonella* spp. (including but not limited to *Salmonella enterica, Salmonella typhi, Salmonella paratyphi, Salmonella enteritidis, Salmonella cholerasuis* and *Salmonella typhimurium*), *Serratia* spp. (including but not limited to *Serratia marcesans* and *Serratia liquifaciens*), *Shigella* spp. (including but not limited to *Shigella dysenteriae, Shigella flexneri, Shigella boydii* and *Shigella sonnei*), *Staphylococcus* spp. (including but not limited to *Staphylococcus aureus, Staphylococcus epidermidis, Staphylococcus hemolyticus, Staphylococcus saprophyticus*), *Streptococcus* spp. (including but not limited to *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistantserotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A streptococci, *Streptococcus pyogenes*, Group B streptococci, *Streptococcus agalactiae*, Group C streptococci, *Streptococcus anginosus, Streptococcus equismilis*, Group D streptococci, *Streptococcus bovis*, Group F streptococci, and *Streptococcus anginosus* Group G streptococci), *Spirillum minus, Streptobacillus moniliformi, Treponema* spp. (including but not limited to *Treponema carateum, Treponema petenue, Treponema pallidum* and *Treponema endemicum, Tropheryma whippelii, Ureaplasma urealyticum, Veillonella* sp., *Vibrio* spp. (including but not limited to *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio furnisii*), *Yersinia* spp. (including but not limited to *Yersinia enterocolitica, Yersinia pestis*, and *Yersinia pseudotuberculosis*) and *Xanthomonas maltophilia* among others.

Furthermore, other infectious agents 106 that can be assayed for anti-infective susceptibility can comprise fungi or mold including, but not limited to, *Candida* spp. (including but not limited to *Candida albicans, Candida glabrata, Candida tropicalis, Candida parapsilosis*, and *Candida krusei*), *Aspergillus* spp. (including but not limited to *Aspergillus fumigatous, Aspergillus flavus, Aspergillus clavatus*), *Cryptococcous* spp. (including but not limited to *Cryptococcus neoformans, Cryptococcus gattii, Cryptococcus laurentii*, and *Cryptococcus albidus*), *Fusarium* spp. (including but not limited to *Fusarium oxysporum, Fusarium solani, Fusarium verticillioides*, and *Fusarium proliferatum*), *Rhizopus oryzae, Penicillium marneffei, Coccidiodes immitis*, and *Blastomyces dermatitidis.*

In some embodiments, the inoculum solution 110 can comprise the infectious agent 106 diluted in a nutrient solution comprising bacto-tryptone, yeast extract, beef extract, cation-adjusted Mueller Hinton Broth (CAMHB), Mueller Hinton (MH) broth, starch, acid hydrolysate of casein, calcium chloride, magnesium chloride, sodium chloride, blood or lysed blood including lysed horse blood (LHB), CAMHB-LHB, glucose, or a combination thereof. In other embodiments, the inoculum solution 110 can also comprise a growth inducer such as a carbon-based inducer, a nitrogen-based inducer, a mineral, a trace element, a biological growth factor, or any combination thereof. For example, the growth inducer can include but is not limited to glucose, ammonia, magnesium, blood, or a combination thereof. In one example embodiment, the inoculum solution 110 can comprise the infectious agent 106, tryptone, yeast extract, sodium chloride, and glucose.

Figure 3A:
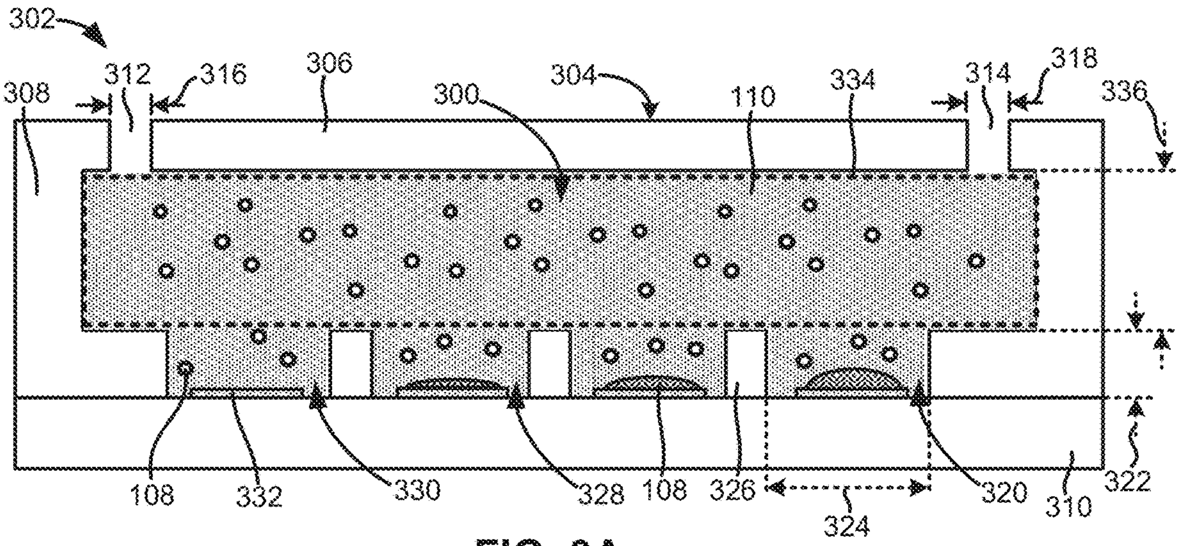
FIGS. 3A and 3B illustrate cross-sectional side views of an embodiment of a sample receiving space of a diagnostic device for determining the susceptibility of an infectious agent to an anti-infective.
Figure 3B:
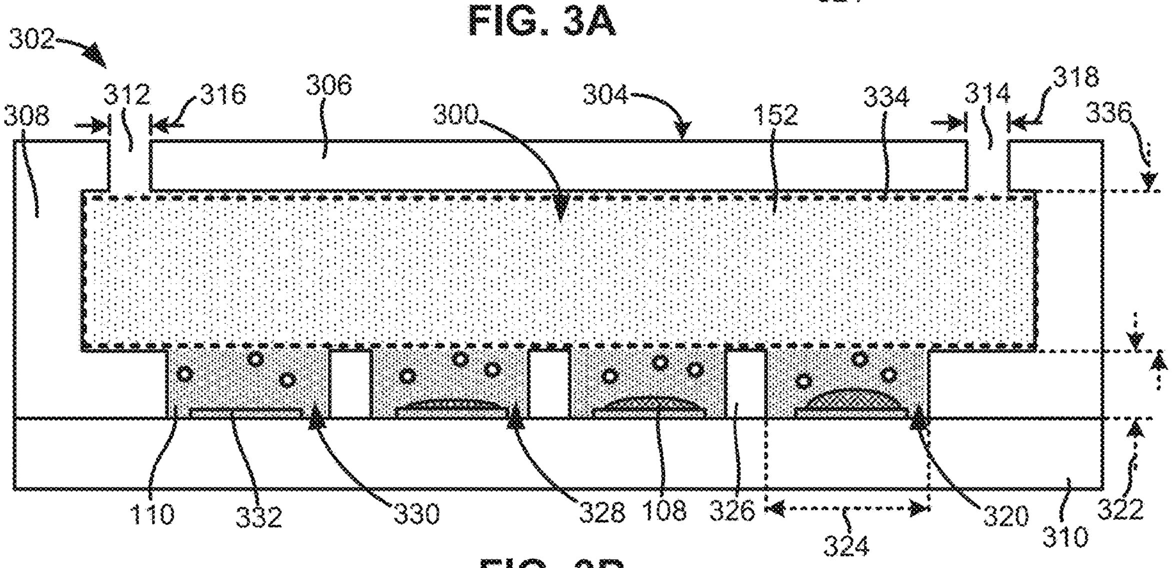
Figure 3C:
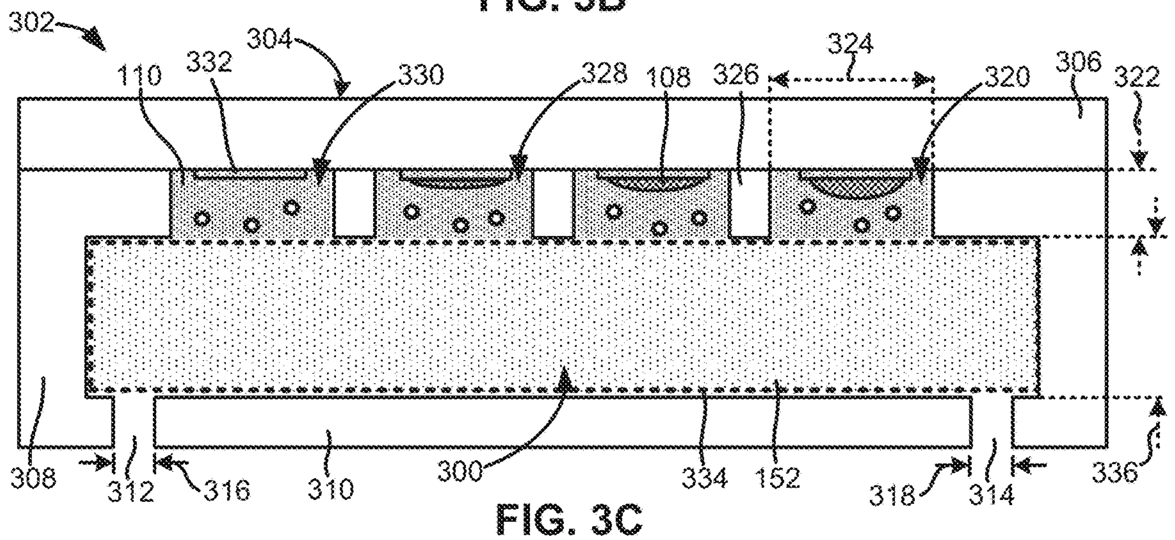
FIG. 3C illustrates a cross-sectional side view of another embodiment of a sample receiving space of the diagnostic device for determining the susceptibility of an infectious agent to an anti-infective.

In other embodiments, the inoculum solution 110 can comprise the infectious agent 106 diluted in deionized water, a saline solution, or a combination of deionized water and a saline solution. In these embodiments, a nutrient solution or growth inducer can be dried or lyophilized on a surface of an electrode as shown in FIGS. 3A-3C.

One or more fluid delivery conduits 116 can inject, deliver, or otherwise introduce the inoculum solution 110 to the sample receiving space 112 of the diagnostic device 102 through the sample inlet port 114. The diagnostic device 102 can also comprise a sample outlet port 118. The sample outlet port 118 can be an opening or conduit in fluid communication with the sample receiving space 112. The one or more fluid delivery conduits 116 can inject, deliver, or otherwise introduce the inoculum solution 110 to the sample receiving space 112 through the sample inlet port 114 and the inoculum solution 110 can flow out of the sample outlet port 118 after filling the sample receiving space 112.

The fluid delivery conduits 116 can comprise or refer to tubes, pumps, containers, channels, passageways, capillaries, microfluidic channels, parts therein, or a combination thereof. For example, as shown in FIG. 1, the fluid delivery conduits 116 can refer to parts of a pump such as a syringe pump. In other embodiments, the fluid delivery conduits 116 can include or refer to at least part of a hydraulic pump, a pneumatic pump, a peristaltic pump, a vacuum pump or a positive pressure pump, a manual or mechanical pump, or a combination thereof. In additional embodiments, the fluid delivery conduits 116 can include or refer to at least part of an injection cartridge, a pipette, a capillary, or a combination thereof. The fluid delivery conduits 116 can also be part of a vacuum system configured to draw fluid to or through channels, tubes, or passageways under vacuum. Moreover, the fluid delivery conduits 116 can include or refer to at least part of a multichannel delivery system or pipette.

The sample receiving space 112 can comprise a plurality of wells 120. In some embodiments, the wells 120 can be substantially bowl-shaped or hemispherical indentations, divots, depressions, or cavities. In other embodiments, the wells 120 can be shaped substantially as a cylinder, an upside-down conic, a frustoconic or upside-down frustoconic, a partial ovoid, or a combination thereof. In additional embodiments, the wells 120 can be substantially cuboid-shaped.

The wells 120 can be fabricated or located on a surface of a substrate layer 122 of the diagnostic device 102. The substrate layer 122 can comprise or be made in part of a non-conductive or inert material. For example, the substrate layer 122 can comprise or be made in part of a polymeric material, a ceramic material or glass, or a combination thereof. As a more specific example, the substrate layer 122 can comprise or be made in part of polyvinyl chloride (PVC), poly(methyl methacrylate) (PMMA), polydimethylsiloxane (PDMS), or a combination thereof. In these and other embodiments, the substrate layer 122 can comprise or be made in part of a semiconductor material and the substrate layer 122 can be part of a chip or circuit board.

The sample receiving space 112 can also comprise a shared space 124. The shared space 124 can be a portion of the sample receiving space 112 in fluid communication with the sample inlet port 114, the sample outlet port 118, and the plurality of wells 120. The shared space 124 can be a cavity or hollow space positioned above or below the plurality of wells 120. As will be discussed in more detail in the following sections, the shared space 124 can be filled or occupied by a water immiscible liquid 152 (see FIGS. 3B and 3C) after the inoculum solution 110 has filled the plurality of wells 120.

The plurality of wells 120 can comprise a plurality of pH electrode wells 126 and a plurality of oxidation reduction potential (ORP) electrode wells 126. Each of the pH electrode wells 126 can comprise a pH electrode 130 and each of the ORP electrode wells 128 can comprise an ORP electrode 132. The pH electrodes 130 and the ORP electrodes 132 can be micro-sized or nano-sized electrodes fabricated or located within the pH electrode wells 126 and the ORP electrode wells 128, respectively. In other embodiments, a pH electrode 130 and an ORP electrode 132 can be fabricated or located within the same well such that each of the plurality of wells 120 comprise both a pH electrode 130 and an ORP electrode 132 without a wall or divider separating the two electrodes.

As will be discussed in more detail in the following sections, the pH electrodes 130 and the ORP electrodes 132 can be connected to a parameter analyzer 156 via one or more conductive connections or conductive traces. Although FIG. 1 shows the pH electrode wells 126 and the ORP electrode wells 128 as separate wells, it is contemplated by this disclosure that a single well 120 can comprise a pH electrode 130 and an ORP electrode 132 in the same well 120. In these embodiments, the pH electrode 130 and the ORP electrode 132 are not separated by a wall or divider.

In some embodiments, each of the pH electrodes 130 can be positioned at or extend out from the bottom of a pH electrode well 126 and each of the ORP electrodes 132 can be positioned at or extend out from the bottom of an ORP electrode well 128 (see FIGS. 3A and 3B). In other embodiments, each of the pH electrodes 130 can be positioned at or extend out from the top of a pH electrode well 126 and each of the ORP electrodes 132 can be positioned at or extend out from the top of an ORP electrode well 128 (see FIG. 3C).

Each of the pH electrodes 130 can comprise or be made in part of a pH sensitive material. In some embodiments, the pH sensitive material can comprise or be made in part of silicon dioxide ($SiO_2$), aluminum oxide ($Al_2O_3$), titanium dioxide ($TiO_2$), tantalum pentoxide ($Ta_2O_5$), hafnium dioxide ($HfO_2$), or a combination thereof. Each of the ORP electrodes 132 can comprise or be made in part of a redox sensitive material. The redox sensitive material can comprise or be made in part of $SiO_2$, $Al_2O_3$, $TiO_2$, $Ta_2O_5$, $HfO_2$, iridium dioxide ($IrO_2$), ruthenium dioxide ($RuO_2$), zirconium dioxide ($ZrO_2$), or a combination thereof. The pH electrodes 130 and the ORP electrodes 132 will be discussed in more detail in the following sections.

At least one of the pH electrode wells 126 and at least one of the ORP electrode wells 128 can be growth control wells 134 devoid of or not comprising the anti-infective 108. The remainder of the pH electrode wells 126 and the remainder of the ORP electrode wells 128 can be active electrode wells 136 each comprising an amount of the anti-infective 108.

The active electrode wells 136 can comprise the anti-infective 108 at differing concentrations. In one embodiment, the active electrode wells 136 can comprise at least a first pH electrode well, a second pH electrode well, a first ORP electrode well, and a second ORP electrode well. The first pH electrode well and the first ORP electrode well can comprise the anti-infective 108 at a first concentration. The second pH electrode well and the second ORP electrode well can comprise the anti-infective 108 at a second concentration. In this example, the first concentration of the anti-infective 108 can be greater than the second concentration. More specifically, the first concentration of the anti-infective 108 can be double the second concentration. In other embodiments, the first concentration of the anti-infective 108 can be triple or quadruple the second concentration.

For example, as shown in FIG. 1, the active electrode wells 136 can comprise the antibiotic Ciprofloxacin at concentrations of 1 μg/mL, 2 μg/mL, 4 μg/mL, 8 μg/mL, 16 μg/mL, 32 μg/mL, etc. Although two anti-infectives 108 (e.g., Levofloxacin and Ciprofloxacin) and a limited number of active electrode wells 136 are shown in FIG. 1, it is contemplated by this disclosure and it should be understood by one of ordinary skill in the art that the diagnostic device 102 can comprise any number of wells 120 including up to 96 wells, 192 wells, or 384 wells and any number of anti-infectives 108 at differing concentrations can be tested and assayed using the methods and systems described herein.

The anti-infectives 108 used in the systems and methods disclosed herein can comprise a bacteriostatic anti-infective, a bactericidal anti-infective, an anti-fungal anti-infective, or a combination thereof.

In certain embodiments, the bacteriostatic anti-infective can comprise β-lactams (including but not limited to penicillins such as ampicillin, amoxicillin, flucloxacillin, penicillin, amoxicillin/clavulanate, and ticarcillin/clavulanate and monobactams such as aztreonam), β-lactam and β-lactam inhibitor combinations (including but not limited to piperacillin-tazobactam and ampicillin-sulbactam), Aminoglycosides (including but not limited to amikacin, gentamicin, kanamycin, neomycin, netilmicin, paromomycin, streptomycin, spectinomycin, and tobramycin), Ansamycins (including but not limited to rifaximin), Carbapenems (including but not limited to ertapenem, doripenem, imipenem, and meropenem), Cephalosporins (including but not limited to ceftaroline, cefepime, ceftazidime, ceftriaxone, cefadroxil, cefalotin, cefazolin, cephalexin, cefaclor, cefprozil, fecluroxime, cefixime, cefdinir, cefditoren, cefotaxime, cefpodoxime, ceftibuten, and ceftobiprole), Chloramphenicols, Glycopeptides (including but not limited to vancomycin, teicoplanin, telavancin, dalbavancin, and oritavancin), Folate Synthesis Inhibitors (including but not limited to trimethoprim-sulfamethoxazole), Fluoroquinolones (including but not limited to ciprofloxacin), Lincosamides (including but not limited to clindamycin, lincomycin, azithromycin, clarithromycin, dirithromycin, roxithromycin, telithromycin, and spiramycin), Lincosamines, Lipopeptides, Macrolides (including but not limited to erythromycin), Monobactams, Nitrofurans (including but not limited to furazolidone and nitrofurantoin), Oxazolidinones (including but not limited to linezolid, posizolid, radezolid, and torezolid), Quinolones (including but not limited to enoxacin, gatifloxacin, gemifloxacin, levofloxacin, lomefloxacin, moxifloxacin, naldixic acid, norfloxacin, trovafloxacin, grepafloxacin, sparfloxacin, and temafloxacin), Rifampins, Streptogramins, Sulfonamides (including but not limited to mafenide, sulfacetamide, sulfadiazine, sulfadimethoxine, sulfamethizole, sulfamethoxazole, sulfasalazine, and sulfisoxazole), Tetracyclines (including but not limited to oxycycline, minocycline, demeclocycline, doxycycline, oxytetracycline, and tetracycline), polypeptides (including but not limited to bacitracin, polymyxin B, colistin, and cyclic lipopeptides such as daptomycin), phages, or a combination or derivative thereof.

In other embodiments, the anti-infective 108 can comprise clofazimine, ethambutol, isoniazid, rifampicin, arsphenamine, chloramphenicol, fosfomycin, metronidazole, tigecycline, trimethoprim, or a combination or derivative thereof.

In certain embodiments, the anti-fungal can comprise Amphotericin B, Anidulafungin, Caspofungin, Fluconazole, Flucytosine, Itraconazole, Ketoconazole, Micafungin, Posaconazole, Ravuconazole, Voriconazole, or a combination or derivative thereof.

In some embodiments, the anti-infective 108 can be dried or lyophilized within the active electrode wells 136. In these embodiments, the anti-infective 108 in dried form or lyophilized form can coat or cover at least part of a well surface (e.g., a well wall surface, well bottom surface, or a combination thereof), an active electrode surface (e.g., a part of the pH electrode or a part of the ORP electrode), or a combination thereof. The anti-infective 108 can be dried or lyophilized within the active electrode wells 136 prior to introducing the inoculum solution 110 into the sample receiving space 112.

In these and other embodiments, the active electrode wells 136 and the growth control wells 134 can also comprise a nutrient solution or a growth inducer in dried (i.e., dehydrated) or lyophilized form within the active electrode wells 136 and the growth control wells 134, respectively. This can be the case when the inoculum solution 110 comprises the infectious agent 106 diluted in deionized water or a saline solution. For example, the active electrode wells 136 can comprise a dried or lyophilized form of a yeast extract, beef extract, cation-adjusted Mueller Hinton Broth (CAMHB), Mueller Hinton (MH) broth, starch, acid hydrolysate of casein, calcium chloride, magnesium chloride, sodium chloride, blood or lysed blood including lysed horse blood (LHB), CAMHB-LHB, glucose, or a combination thereof.

The inoculum solution 110 can re-hydrate the dried or lyophilized anti-infective 108 when the inoculum solution 110 flows into the plurality of active electrode wells 136 (including the plurality of pH electrode wells 126 and the plurality of ORP electrode wells 128). The inoculum solution 110 can be in fluid communication with the pH electrode 130 (including the pH sensitive material) within each of the pH electrode wells 126 when the inoculum solution 110 fills the pH electrode wells 126. Moreover, the inoculum solution 110 can be in fluid communication with the ORP electrode 132 (including the redox sensitive material) within each of the ORP electrode wells 128 when the inoculum solution 110 fills the ORP electrode wells 128. Once the inoculum solution 110 has filled the plurality of wells 120, the excess inoculum solution 110 can flow out of the sample outlet port 118.

The diagnostic device 102 can also comprise a buffer receiving space 138 comprising a plurality of reference electrode wells 140. Each of the reference electrode wells 140 can comprise a reference electrode 142. The reference electrode 142 can comprise or be made in part of platinum, gold, stainless steel, or a combination thereof. In some embodiments, the reference electrode 142 can be positioned or extend from the bottom of the reference electrode well 140. In other embodiments, the reference electrode 142 can be positioned or extend from the top of the reference electrode well 140. The reference electrode wells 140 can be sized and shaped substantially similar to the wells 120 within the sample receiving space 112.

Each of the reference electrode wells 140 can be in fluid communication with at least one pH electrode well 126 and at least one ORP electrode well 128 via a connecting conduit 144. The connecting conduit 144 can refer to a channel, passageway, or capillary connecting each of the reference electrode wells 140 to at least one pH electrode well 126 and at least one ORP electrode well 128. For example, the connecting conduit 144 can be a microfluidic channel.

The method 100 can further comprise introducing a reference buffer 146 into the buffer receiving space 138 through a buffer inlet port 148 of the diagnostic device 102 in step 1B. The reference buffer 146 can be introduced into the buffer receiving space 138 using one or more fluid delivery conduits 116. The reference buffer 146 can fill the plurality of reference electrode wells 140 and at least part of the connecting conduits 144 upon being introduced into the buffer receiving space 138. Any excess reference buffer 146 can flow out of a buffer outlet port 150 of the diagnostic device 102 once it has filled the buffer receiving space 138.

When the reference buffer 146 has filled the reference electrode wells 140 and at least part of the connecting conduits 144, the reference buffer 146 can act as a salt bridge or liquid bridge connecting the reference buffer 146 within the reference electrode wells 140 to the inoculum solution 110 within the pH electrode wells 126 and the ORP electrode wells 128. The reference buffer 146 can allow the reference electrodes 142 to be in ion exchange contact with the inoculum solution 110 within the pH electrode wells 126, the ORP electrode wells 128, or a combination thereof.

In some embodiments, the reference buffer 146 can be or comprise an aqueous reference buffer solution. In some embodiments, the aqueous reference buffer solution can be an aqueous redox buffer solution comprising deionized water (e.g., about 95%-99%), potassium hexacyanoferrate (III) (e.g., about 0.1% to 0.9%), potassium hexacyanoferrate (II) (e.g., about 0.1% to 0.9%), potassium dihydrogen phosphate (e.g., less than about 0.5%), and disodium hydrogen phosphate (less than about 0.5%). As a more specific example, the aqueous reference buffer solution can be a 220 mV/pH 7 redox buffer solution (Product Code 51350060) provided by Mettler-Toledo AG.

In other embodiments, the aqueous reference buffer solution can be or comprise a redox buffer solution comprising 3M KCl. As a more specific example, the aqueous reference buffer solution can be a 3M KCl redox buffer solution (Material No. 63056165) provided by Mettler-Toledo AG.

In other embodiments, the reference buffer 146 can be a reference buffer gel. The reference buffer gel can comprise the aqueous reference buffer solution and a thickening agent. In some embodiments, the thickening agent can be agar powder. In other embodiments, the thickening agent can comprise a polysaccharide or polysaccharide powder. As a more specific example, the agar powder used can be a commercially available agar powder such as agar powder provided by Sigma-Aldrich, Inc. (e.g., Sigma-Aldrich™ Agar Powder 05040) or Thermo Fisher Scientific Inc. (e.g., Fisher Scientific™ Agar Powder, Catalog No. S14153).

In one embodiment, the reference buffer gel can comprise the thickening agent at a concentration of about 1% (w/v %, g/mL). In another embodiment, the reference buffer gel can comprise the thickening agent at a concentration of about 5% (w/v %, g/mL). In some embodiments, the reference buffer gel can comprise the thickening agent at a concentration of between about 1% (w/v %, g/mL) and 5% (w/v %, g/mL). In other embodiments, the reference buffer gel can comprise the thickening agent at a concentration of between about 5% (w/v %, g/mL) and 10% (w/v %, g/mL).

The reference buffer gel can be made by heating the aqueous reference buffer solution above the boiling point of the aqueous reference buffer solution and stirring the thickening agent into the heated aqueous reference buffer solution. Once the thickening agent (e.g., the agar powder) is completely dissolved in the heated aqueous reference buffer solution, the hot gel slurry can be introduced into the buffer inlet port 148 via the buffer inlet port 148. The hot gel slurry can fill or otherwise occupy the buffer receiving space 138 including the reference electrode wells 140. The hot gel slurry can also fill or otherwise occupy at least part of the connecting conduits 144. The hot gel slurry can be allowed to cool to room temperature and solidify at room temperature. Once the hot gel slurry is solidified, the reference buffer gel can fill or otherwise occupy the reference electrode wells 140 and at least part of the connecting conduits 144.

The method 100 can further comprise introducing a water immiscible liquid 152 into the sample receiving space 112 through the sample inlet port 114 in step 1C. The water immiscible liquid 152 can be introduced, delivered, or otherwise injected into the sample receiving space 112 using one or more fluid delivery conduits 116.

The water immiscible liquid 152 can seal the plurality of wells 120 comprising the inoculum solution 110 and prevent the anti-infective 108 within the active electrode wells 136 from flowing out of their respective well cavities, thereby affecting the concentration of the anti-infective 108 within the other active electrode wells 136. Sealing the plurality of wells 120 comprising the inoculum solution 110 can also prevent the growth control wells 134 from being contaminated by the anti-infective 108 from the active electrode wells 136. The water immiscible liquid 152 can also prevent contaminants from entering the plurality of wells 120 once the wells 120 are filled with the inoculum solution 110.

The water immiscible liquid 152 can seal the plurality of wells 120 by filling and occupying the shared space 124. The water immiscible liquid 152 can displace any inoculum solution 110 previously within the shared space 124 out of the sample receiving space 112 through the sample outlet port 118 or push the inoculum solution 110 previously within the shared space 124 into the wells 120. In this manner, the water immiscible liquid 152 can ensure the contents within each of the wells 120 do not disturb measurements within neighboring wells 120.

One advantage of adding the water immiscible liquid 152 after the inoculum solution 110 has been introduced into the plurality of wells 120 is that the water immiscible liquid 152 does not significantly displace the inoculum solution 110 in fluid contact with the electrodes (e.g., the pH electrodes 130 and the ORP electrodes 132) within the wells 120. One explanation could be that the hydrophilic inoculum solution 110 is drawn more to the pH sensitive material of the pH electrodes 130 and the redox sensitive material of the ORP electrodes 132 than the hydrophobic water immiscible liquid 152. As such, the water immiscible liquid 152 acts to seal or cover the entrance or openings to the wells 120 containing the inoculum solution 110.

The water immiscible liquid 152 can be a hydrophobic oil or solvent. In some embodiments, the water immiscible liquid 152 can be silicone oil, a non-polar solvent, or a combination thereof. The water immiscible liquid 152 can be gas permeable and allow oxygen and carbon dioxide to permeate through the water immiscible liquid 152.

The method 100 can also comprise incubating the diagnostic device 102 comprising the inoculum solution 110 and the water immiscible liquid 152 at an elevated temperature for a predetermined time period 154 in step 1D. In some embodiments, the diagnostic device 102 can be incubated by being heated to a temperature of between about 30° C. and about 40° C. (e.g., 35° C.±2° C.).

In these and other embodiments, the diagnostic device 102 can be allowed to incubate at the elevated temperature for between about 15 minutes and 60 minutes. In other embodiments, the diagnostic device 102 can be allowed to incubate at the elevated temperature for between about 60 minutes and 120 minutes. In additional embodiments, the diagnostic device 102 can be allowed to incubate at the elevated temperature for between about 120 minutes and 240 minutes. In further embodiments, the diagnostic device 102 can be allowed to incubate at the elevated temperature for between about 240 minutes and 480 minutes. In certain embodiments, the diagnostic device 102 can be allowed to incubate at the elevated temperature for between about 480 minutes and up to about 48 hours.

The predetermined time period 154 (or the incubation period) can be adjusted based on the type of infectious agent 106 suspected in the inoculum solution 110, such as the type of bacteria or fungus. The predetermined time period 154 can also be adjusted based on the type of anti-infective 108, the mechanism of action of the anti-infective 108, the amount of the inoculum solution 110 introduced into the diagnostic device 102, or a combination thereof. The predetermined time period 154 (or the incubation period) can be start-delayed or a pre-incubation time period can be added before the start of the incubation period. The start-delay or the pre-incubation time period can be added for slower acting drugs or anti-infectives 108 (e.g., beta-lactams). In some embodiments, the start-delay or the pre-incubation time period can be between 10 minutes and 2 hours. In other embodiments, the start-delay or the pre-incubation time period can be as long as needed for the drug or anti-infective 108 to take effect. During the start-delay or pre-incubation time period, readings or measurements from the electrodes would not be used or would not be included as part of any growth curves generated (pH or ORP signals monitored). The start-delay or the pre-incubation time period is particularly useful for instances where higher concentrations of the infectious agent 106 is present in the inoculum solution 110 and where the signal is generated relatively fast in comparison to the mode of action of the drug or anti-infective 108.

The method 100 can further comprise an optional step of identifying a species or other classification type or characteristic of the infectious agent 106 in the inoculum solution 110. In addition to species, the other classification type can comprise a genus, a family, an order, a class, a phylum, a kingdom, and a domain of the infectious agent 106 in the inoculum solution 110.

In some embodiments, identifying the species or other classification type of the infectious agent 106 can involve receiving such information from a user via an input device (e.g., a keyboard or touchscreen) coupled to a computing device 158 of the system 104. In other embodiments, identifying the species or other classification type of the infectious agent 106 can involve receiving such information from another computing device communicatively coupled to the computing device 158 or retrieving such information from a database. The classification-type (e.g., the species, the genus, the family, etc.) or the characteristic of the infectious agent 106 can be stored in a memory of the computing device 158, a computing cloud, or a remote server accessible to the computing device 158 over a network.

In some embodiments, identifying the species of the infectious agent 106 in the inoculum solution 110 can involve determining the species using a biochemical test (e.g., a test for metabolism or a test for specific enzymes), mass spectrometry, genotyping, phenotypic analysis from culture plates, test kits comprising phages, or a combination thereof. In other embodiments, the characteristic of the infectious agent 106 can be a response of the infectious agent 106 to a Gram stain test. For example, the method 100 can comprise performing a Gram stain test and identifying the infectious agent 106 as Gram-positive or Gram-negative bacteria. In certain embodiments, the species of the infectious agent 106 in the inoculum solution 110 can be identified but the particular strain of the infectious agent 106 can be left unknown. As previously discussed, the incubation period can be adjusted based on the species of the infectious agent 106 in the inoculum solution 110.

The method 100 can also comprise monitoring one or more solution characteristics of the inoculum solution 110 within the active electrode wells 136 and the growth control wells 134 over the predetermined time period 154 in step 1E. In some embodiments, monitoring one or more solution characteristics of the inoculum solution 110 within the active electrode wells 136 and the growth control wells 134 can be done while the diagnostic device 102 is being incubated at the elevated temperature.

The one or more solution characteristics monitored can comprise the pH of the inoculum solution 110, the ORP of the inoculum solution 110, and both the pH and the ORP of the inoculum solution 110. In some embodiments, the one or more solution characteristics can be monitored without or in the absence of any reporter molecules or exogenous reporter molecules added to the inoculum solution 110.

The solution characteristic of the inoculum solution 110 within the active electrode wells 136 and the growth control wells 134 can change as the amount of ions or the amount of electro-active redox species in solution changes due to the energy use, oxygen uptake or release, growth, or metabolism of the infectious agent 106 in the active electrode wells 136 and the growth control wells 134. For example, the amount of electro-active redox species in solution in the active electrode wells 136 and the growth control wells 134 can change because of cellular activity (e.g., microbial aerobic or anaerobic respiration) undertaken by the infectious agents 106 in the active electrode wells 136 and the growth control wells 134. Also, as an example, the amount of $H^+$ ions in the inoculum solution 110 can change as a result of cellular activity undertaken by the infectious agents 106 in solution in the various active electrode wells 136 and the growth control wells 134.

As a more specific example, the amount of electron donors from Table 1 below (e.g., the amount of energy carriers such as nicotinamide adenine dinucleotide (NADH) and flavin adenine dinucleotide ($FADH_2$)) in the inoculum solution 110 in the various active electrode wells 136 and the growth control wells 134 can change due to the growth of the infectious agent 106 in solution in such wells. Also, as another more specific example, the amount of oxygen depleted in the inoculum solution 110 due to aerobic respiration can change due to the growth of the infectious agent 106 in solution.

TABLE 1

Below is a "redox tower" visualizing potential electron donors and acceptors which can be utilized by infectious agents during the course of metabolism. An electron donor will have a greater negative potential than the electron acceptor. In aerobic respiration for example, $O_2$ can serve as a terminal electron acceptor whereas in anaerobic respiration, the terminal electron acceptor can comprise $NO_3^-$, $Fe^{3+}$, $Mn^{4+}$, $SO_4^{2-}$, or $CO_2$.

| Electron Donor and Acceptor Pairs | Measured Standard Reduction Potential E'$_0$ (mV) | Standard Reduction Potential E'$_0$ (mV) range |
|---|---|---|
| Glucose ⇆ 2 Pyruvate + $2e^-$ | −720 | −700 |
| | | −600 |
| Glucose ⇆ 6 $CO_2$ + $24e^-$ | −500 | −500 |
| $H_2$ ⇆ $2H^+$ + $2e^-$ | −420 | −400 |
| NADH ⇆ $NAD^+$ + $2e^-$ | −320 | −300 |
| 2 GSH ⇆ GSSG + $2e^-$ | −240 | −200 |

TABLE 1-continued

Below is a "redox tower" visualizing potential electron donors and acceptors which can be utilized by infectious agents during the course of metabolism. An electron donor will have a greater negative potential than the electron acceptor. In aerobic respiration for example, $O_2$ can serve as a terminal electron acceptor whereas in anaerobic respiration, the terminal electron acceptor can comprise $NO_3^-$, $Fe^{3+}$, $Mn^{4+}$, $SO_4^{2-}$, or $CO_2$.

| Electron Donor and Acceptor Pairs | Measured Standard Reduction Potential E'$_0$ (mV) | Standard Reduction Potential E'$_0$ (mV) range |
|---|---|---|
| $H_2$ ⇆ $SO_4^{2-}$ + $8e^-$ | −220 | |
| $FADH_2$ ⇆ FAD + $2H^+$ + $2e^-$ | −220 | |
| Lactate ⇆ Pyruvate + $2e^-$ | −190 | −100 |
| Succinate ⇆ Fumarate + $2e^-$ | 33 | 0 |
| Cyt b (red) ⇆ Cyt b (ox) + $e^-$ | 80 | |
| Ubiquinol ⇆ Ubiquinone + $2e^-$ | 110 | 100 |
| Cyt c (red) ⇆ Cyt c (ox) + $e^-$ | 250 | 200 |
| Cyt a (red) ⇆ Cyt a (ox) + $e^-$ | 290 | |
| | | 300 |
| $NO_2^-$ + $H_2O$ ⇆ $NO_3^-$ + $2e^-$ | 420 | 400 |
| $NH_4^+$ $H_2O$ ⇆ $NO_2^-$ + $6e^-$ | 440 | |
| $Mn^{2+}$ $H_2O$ ⇆ $MnO_2$ + $2e^-$ | 460 | |
| | | 500 |
| | | 600 |
| 12 $N_2$ + $3H_2O$ ⇆ $NO_3^-$ + $5e^-$ | 740 | 700 |
| $Fe^{2+}$ ⇆ $Fe^{3+}$ + $1e^-$ | 770 | |
| $H_2O$ ⇆ ½ $O_2$ + $2H^+$ + $2e^-$ | 820 | 800 |
| | | 700 |

The method 100 can further comprise comparing the one or more solution characteristics of the inoculum solution 110 within the growth control wells 134 with the one or more solution characteristics of the inoculum solution 110 within the various active electrode wells 136 to determine the minimum inhibitory concentration (MIC) of the anti-infective 108 on the infectious agent 106 in step 1F. For example, when the solution characteristic of the inoculum solution 110 monitored is pH, the MIC of the anti-infective 108 on the infectious agent 106 can be determined by comparing the pH of the inoculum solution 110 within the growth control wells 134 comprising the pH electrodes 130 with the pH of the inoculum solution 110 within the various active electrode wells 136 comprising the pH electrodes 130.

As another example, when the solution characteristic of the inoculum solution 110 monitored is the ORP of the solution, the MIC of the anti-infective 108 on the infectious agent 106 can be determined by comparing the ORP of the inoculum solution 110 within the growth control wells 134 with the ORP of the inoculum solution 110 within the various active electrode wells 136. In this example embodiment, each of the growth control wells 134 and each of the active electrode wells 136 can comprise an ORP electrode 132.

In an additional example, when the solution characteristic of the inoculum solution 110 monitored is both pH and ORP, the MIC of the anti-infective 108 on the infectious agent 106 can be determined by comparing the pH and ORP of the inoculum solution 110 within the growth control wells 134 with the pH and ORP of the inoculum solution 110 within the various active electrode wells 136. In this example embodiment, each of the growth control wells 134 and each of the active electrode wells 136 can comprise both a pH electrode 130 and an ORP electrode 132.

In some embodiments, monitoring the one or more solution characteristics of the inoculum solution 110 within the growth control wells 134 and the one or more solution characteristics of the inoculum solution 110 within the active electrode wells 136 can be done using one or more parameter analyzers 156. The one or more parameter analyzers 156 can be coupled to the pH electrodes 130 the ORP electrodes 132 within the growth control wells 134 and the pH electrodes 130 and the ORP electrodes 132 within the active electrode wells 136. The one or more parameter analyzers 156 can also be coupled to the reference electrodes 142 within the reference electrode wells 140.

The pH of the inoculum solution 110 can be determined using the parameter analyzer 156 based on a difference between the potential measured at an active electrode (e.g., one of the pH electrodes 130) and the potential measured at a reference electrode 142. Similarly, the ORP of the inoculum solution 110 can be determined using the parameter analyzer 156 based on a difference between the potential measured at an active electrode (e.g., one of the ORP electrodes 132) and the potential measured at a reference electrode 142.

In certain embodiments, the one or more parameter analyzers 156 can be or refer to one or more voltmeters, multimeters, or other voltage-measurement apparatus. In some embodiments, the one or more parameter analyzers 156 can be integrated with the diagnostic device 102. For example, the one or more parameter analyzers 156 can comprise one or more chips or circuitry fabricated on the substrate layer 122 of the diagnostic device 102. In other embodiments, the one or more parameter analyzers 156 can be standalone devices such as standalone voltmeters or multimeters. The parameter analyzers 156 can be electrically coupled to the pH electrodes 130, the ORP electrodes 132, and the reference electrodes 142 via conductive wires, traces, other conductive connections, or a combination thereof.

The parameter analyzer 156 can also be coupled, either directly or communicatively, to a computing device 158. The diagnostic device 102, the one or more parameter analyzers 156 and the computing device 158 can be part of the system 104. In some embodiments, the parameter analyzer 156 and the computing device 158 can be integrated into one device or apparatus. In other embodiments, the parameter analyzer 156 can be integrated with the diagnostic device 102 (e.g., fabricated on a surface or substrate layer 122 of the diagnostic device 102) and the entire diagnostic device 102 can be detachably coupled via one or more hardware interfaces or connections to the computing device 158. In these embodiments, the computing device 158 can act as a reader of the diagnostic device 102. For example, the diagnostic device 102 can be configured as a cartridge, a test strip, a microfluidic chip or device, a lab-on-a-chip (LOC) device, a micro-electro-mechanical system (MEMS) device, a portion therein, or a combination thereof.

In some embodiments, the computing device 158 can be or refer to a desktop computer, a laptop computer, a tablet device, a mobile device, a handheld device, or a combination thereof. In other embodiments, the computing device 158 can be or refer to a server, a computing node, a cloud computing resource, or a combination thereof. The computing device 158 can comprise a display such as a desktop monitor, a laptop monitor, a tablet display, a mobile display, or a combination thereof. In additional embodiments, the computing device 158 can be any device comprising one or more processors, a memory, a display or display interface, and a hardware interface configured to couple and communicate with the parameter analyzer 156.

The parameter analyzer 156, the computing device 158, or a combination thereof can monitor the one or more solution characteristics of the inoculum solution 110 within the growth control wells 134 and the one or more solution characteristics of the active electrode wells 136 by generating one or more infectious agent growth curves 160 tracking the change in the solution characteristics. For example, the infectious agent growth curves 160 can be bacterial growth curves or fungi growth curves. The infectious agent growth curves 160 can track the change in pH of the inoculum solution 110, the change in the ORP of the inoculum solution 110, or a combination thereof over time.

As previously discussed, the method 100 can further comprise comparing the one or more solution characteristics of the inoculum solution 110 within the growth control wells 134 with the one or more solution characteristics of the inoculum solution 110 within the active electrode wells 136 to determine the minimum inhibitory concentration (MIC) of the anti-infective 108 on the infectious agent 106. Comparing the one or more solution characteristics of the inoculum solution 110 within the growth control wells 134 with the one or more solution characteristics of the inoculum solution 110 within the active electrode wells 136 can be done using the parameter analyzer 156, the computing device 158 coupled to the parameter analyzer 156, or a combination thereof.

In some embodiments, the computing device 158, the parameter analyzer 156, or a combination thereof can compare the infectious agent growth curves 160 generated from the monitored inoculum solutions 110 within the growth control wells 134 with the infectious agent growth curves 160 generated from the monitored inoculum solutions 110 within the active electrode wells 136. As previously discussed, the active electrode wells 136 can comprise the anti-infective 108 at differing concentrations. For example, the infectious agent growth curves 160 can be compared based on at least one of a (1) time to a pH threshold, (2) a length of an initial lag time, (3) a slope of an exponential phase of the growth curve, (4) a time to a stationary phase of the growth curve, (5) a total curve amplitude, and (6) an area under the curve.

For example, as shown in FIG. 1, the anti-infective 108 assayed can be Ciprofloxacin and the active electrode wells 136 (including pH electrode wells 126 and ORP electrode wells 128) can comprise Ciprofloxacin at concentrations of 1 μg/mL, 2 μg/mL, 4 μg/mL, 8 μg/mL, 16 μg/mL, and 32 μg/mL. In this example, the inoculum solution 110 can be determined to comprise the bacteria *Escherichia coli* (*E. coli*). Bacterial growth curves can be generated from the change in solution characteristics of the inoculum solution 110 present in each of the growth control wells 134 (including at least one pH electrode well 126 and at least one ORP electrode well 128 without Ciprofloxacin) and the active electrode wells 136 (comprising Ciprofloxacin at the aforementioned concentrations). The bacterial growth curves generated can include pH growth curves, ORP growth curves, or a combination thereof.

The various bacterial growth curves generated from measurements of the inoculum solutions 110 within the active electrode wells 136 can then be compared to the bacterial growth curves generated from measurements of the inoculum solutions 110 within the growth control wells 134. The computing device 158, the parameter analyzer 156, or a combination thereof can compare the bacterial growth curves based on one or more of the following curve attributes: (1) time to a pH threshold, (2) a length of an initial lag time, (3) a slope of an exponential phases of the growth curve, (4) a time to a stationary phase of the growth curve, (5) a total curve amplitude, and (6) an area under the curve. If the parameter analyzer 156, the computing device 158, or a combination thereof determined that the bacterial growth curves of active electrode wells 136 comprising a Ciprofloxacin concentration of less than or equal to 8 μg/mL did not differ significantly (i.e., no statistically significant difference) from the bacterial growth curves of the growth control wells 134 then this particular strain of *E. coli* in the inoculum solution 110 would be considered resistant to Ciprofloxacin at such concentrations. Moreover, if the parameter analyzer 156, the computing device 158, or a combination thereof determined that the bacterial growth curves of active electrode wells 136 comprising a Ciprofloxacin concentration of 16 μg/mL did differ significantly (i.e., exhibits a statistically significant difference) from the bacterial growth curves of the growth control wells 134, then this particular strain of *E. coli* in the inoculum solution 110 would be considered susceptible to Ciprofloxacin at such concentrations and above. In this case, the MIC of Ciprofloxacin on this particular strain of *E. coli* in the inoculum solution 110 would be determined to be 16 μg/mL.

In some embodiments, one or more of the aforementioned steps of the method 100 can be stored as machine-executable instructions or logical commands in a non-transitory machine-readable medium (e.g., a memory or storage unit) of the parameter analyzer 156, the computing device 158, or another device communicatively or electrically coupled to the parameter analyzer 156 or the computing device 158. Any of the parameter analyzer 156, the computing device 158, or another device coupled to the parameter analyzer 156 or the computing device 158 can comprise one or more processors or controllers configured to execute the aforementioned instructions or logical commands.

The steps depicted in FIG. 1 do not require the particular order shown to achieve the desired result. Moreover, certain steps or processes may be omitted or occur in parallel in order to achieve the desired result. In addition, any of the systems or devices disclosed herein can be used in lieu of devices or systems shown in the steps of FIG. 1.

Figure 2:
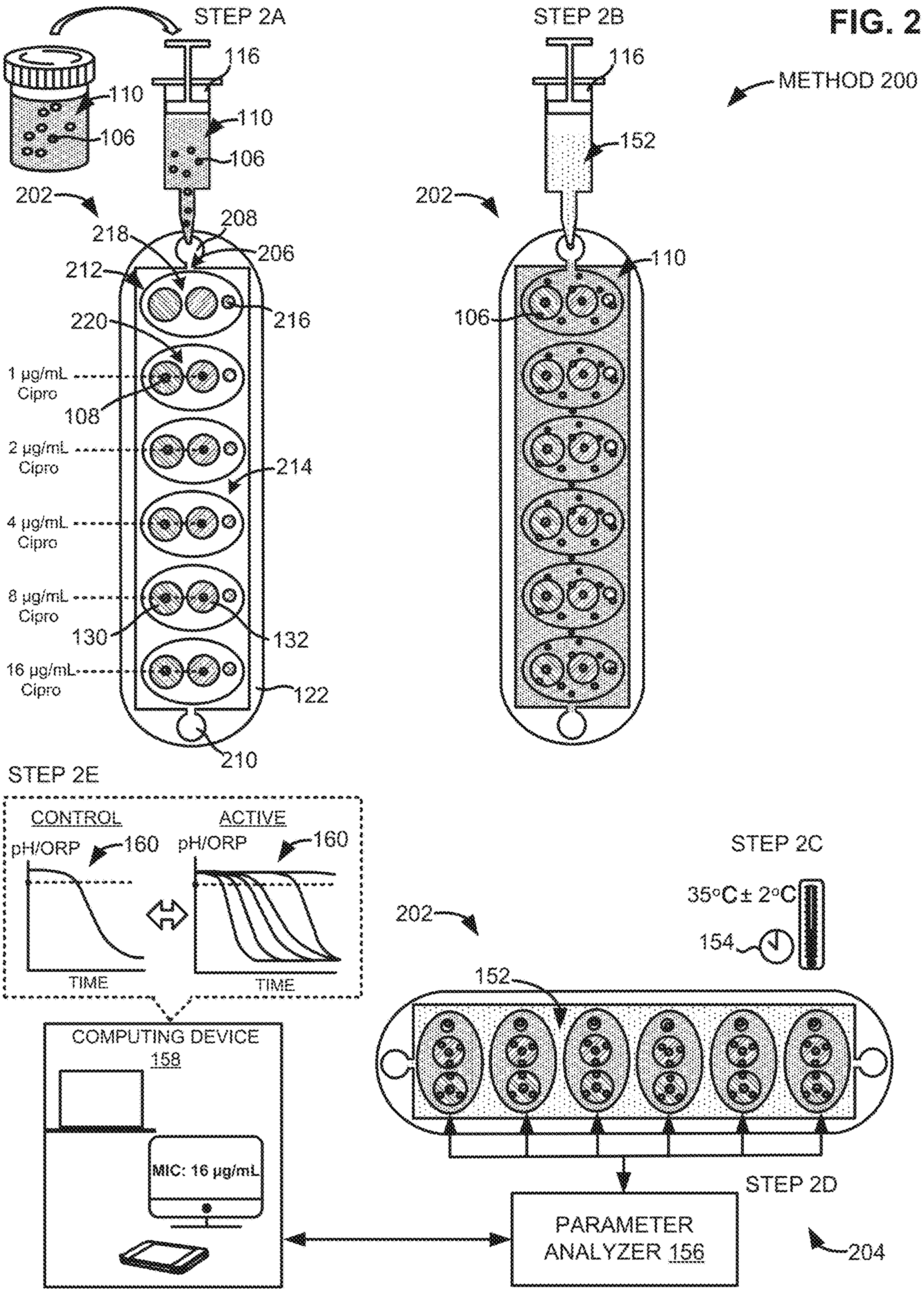
FIG. 2 illustrates other embodiments of a method, diagnostic device, and system for determining the susceptibility of an infectious agent to an anti-infective.

FIG. 2 illustrates other embodiments of a method 200, diagnostic device 202, and system 204 for determining the susceptibility of an infectious agent 106 to an anti-infective 108. The method 200 can comprise introducing the inoculum solution 110 comprising the infectious agent 106 into a sample receiving space 206 of the diagnostic device 202 through a sample inlet port 208 of the diagnostic device 202 in step 2A. The sample inlet port 208 can be an opening or conduit in fluid communication with the sample receiving space 206.

In some embodiments, the inoculum solution 110 can comprise the infectious agent 106 diluted in a nutrient solution comprising bacto-tryptone, yeast extract, beef extract, cation-adjusted Mueller Hinton Broth (CAMHB), Mueller Hinton (MH) broth, starch, acid hydrolysate of casein, calcium chloride, magnesium chloride, sodium chloride, blood or lysed blood including lysed horse blood (LHB), CAMHB-LHB, glucose, or a combination thereof. In other embodiments, the inoculum solution 110 can also comprise a growth inducer such as a carbon-based inducer, a nitrogen-based inducer, a mineral, a trace element, a biological growth factor, or any combination thereof. For example, the growth inducer can include but is not limited to glucose, ammonia, magnesium, blood, or a combination thereof. In one example embodiment, the inoculum solution 110 can comprise the infectious agent 106, tryptone, yeast extract, sodium chloride, and glucose.

In other embodiments, the inoculum solution 110 can comprise the infectious agent 106 diluted in deionized water, a saline solution, or a combination of deionized water and a saline solution. In these embodiments, a nutrient solution or growth inducer can be dried or lyophilized on a surface of an electrode as shown in FIGS. 3A-3C.

One or more fluid delivery conduits 116 can inject, deliver, or otherwise introduce the inoculum solution 110 to the sample receiving space 206 of the diagnostic device 202 through the sample inlet port 208. The diagnostic device 202 can also comprise a sample outlet port 210. The sample outlet port 210 can be an opening or conduit in fluid communication with the sample receiving space 206. The one or more fluid delivery conduits 116 can inject, deliver, or otherwise introduce the inoculum solution 110 to the sample receiving space 206 through the sample inlet port 208 and the inoculum solution 110 can flow out of the sample outlet port 210 after filling the sample receiving space 206.

The sample receiving space 206 can comprise a plurality of wells 212. In some embodiments, the wells 212 can be substantially bowl-shaped or ovoid-shaped indentations, divots, depressions, or cavities. In other embodiments, the wells 212 can be shaped substantially as a cylinder, an upside-down conic, a frustoconic or upside-down frustoconic, a hemisphere or partial sphere, or a combination thereof. In additional embodiments, the wells 212 can be substantially cuboid-shaped.

The wells 212 can be fabricated or located on a surface of a substrate layer 122 of the diagnostic device 202. The substrate layer 122 can comprise or be made in part of a non-conductive or inert material. For example, the substrate layer 122 can comprise or be made in part of a polymeric material, a ceramic material or glass, or a combination thereof. As a more specific example, the substrate layer 122 can comprise or be made in part of polyvinyl chloride (PVC), poly(methyl methacrylate) (PMMA), polydimethylsiloxane (PDMS), or a combination thereof. In these and other embodiments, the substrate layer 122 can comprise or be made in part of a semiconductor material and the substrate layer 122 can be part of a chip or circuit board.

The sample receiving space 206 can also comprise a shared space 214. The shared space 214 can be a portion of the sample receiving space 206 in fluid communication with the sample inlet port 208, the sample outlet port 210, and the plurality of wells 212. The shared space 214 can be a cavity or hollow space positioned above or below the plurality of wells 212. As will be discussed in more detail in the following sections, the shared space 214 can be filled or occupied by a water immiscible liquid 152 (see FIGS. 3B and 3C) after the inoculum solution 110 has filled the plurality of wells 212.

Each of the plurality of wells 212 can comprise at least one pH electrode 130, at least one ORP electrode 132, and at least one solid-state reference electrode 216. The pH electrode 130, the ORP electrode 132, and the solid-state reference electrode 216 can be micro-sized or nano-sized electrodes fabricated or located within the wells 212. As will be discussed in more detail in the following sections, the pH electrodes 130, the ORP electrodes 132, and the solid-state reference electrodes 216 can be connected to a parameter analyzer 156 via one or more conductive connections or conductive traces.

In some embodiments, each of the pH electrodes 130, the ORP electrodes 132, and the solid-state reference electrodes 216 can be positioned at or extend out from the bottom of a well 212 (see FIGS. 3A and 3B). In other embodiments, each of the pH electrodes 130, the ORP electrodes 132, and the solid-state reference electrodes 216 can be positioned at or extend out from the top of a well 212 (see FIG. 3C).

Each of the pH electrodes 130 can comprise or be made in part of a pH sensitive material. In some embodiments, the pH sensitive material can comprise or be made in part of silicon dioxide ($SiO_2$), aluminum oxide ($Al_2O_3$), titanium dioxide ($TiO_2$), tantalum pentoxide ($Ta_2O_5$), hafnium dioxide ($HfO_2$), or a combination thereof. Each of the ORP electrodes 132 can comprise or be made in part of a redox sensitive material. The redox sensitive material can comprise or be made in part of $SiO_2$, $Al_2O_3$, $TiO_2$, $Ta_2O_5$, $HfO_2$, iridium dioxide ($IrO_2$), ruthenium dioxide ($RuO_2$), zirconium dioxide ($ZrO_2$), or a combination thereof. The pH electrodes 130 and the ORP electrodes 132 will be discussed in more detail in the following sections.

At least one of the wells 212 can be growth control wells 218 devoid of or not comprising the anti-infective 108. The growth control wells 218 can be one or more wells selected out of the plurality of wells 212 not containing the anti-infective 108. The remainder of the wells 212 can be active electrode wells 220 comprising the anti-infective 108. The active electrode wells 220 can comprise the anti-infective 108 at differing concentrations.

For example, the active electrode wells 220 can comprise at least a first well and a second well. The first well can comprise the anti-infective 108 at a first concentration. The second well can comprise the anti-infective 108 at a second concentration. In this example, the first concentration of the anti-infective 108 can be greater than the second concentration. More specifically, the first concentration of the anti-infective 108 can be double the second concentration. In other embodiments, the first concentration of the anti-infective 108 can be triple or quadruple the second concentration.

For example, as shown in FIG. 2, the active electrode wells 220 can comprise the antibiotic Ciprofloxacin at concentrations of 1 μg/mL, 2 μg/mL, 4 μg/mL, 8 μg/mL, 16 μg/mL, etc. Although one anti-infective (e.g., Ciprofloxacin) and five pairs of active electrode wells 220 are shown in FIG. 2, it is contemplated by this disclosure and it should be understood by one of ordinary skill in the art that the diagnostic device 202 can comprise any number of wells 212 including up to 96 wells, 192 wells, or 384 wells and multiple anti-infectives 108 of differing concentrations can be tested and assayed using the methods and systems described herein.

In some embodiments, the anti-infective 108 can be dried or lyophilized within the active electrode wells 220. In these embodiments, the anti-infective 108 in dried form or lyophilized form can coat or cover at least part of a well surface (e.g., a well wall surface, well bottom surface, or a combination thereof), an active electrode surface (e.g., a part of the pH electrode or a part of the ORP electrode), or a combination thereof. The anti-infective 108 can be dried or lyophilized within the active electrode wells 220 prior to introducing the inoculum solution 110 into the sample receiving space 206.

In these and other embodiments, the active electrode wells 220 and the growth control wells 218 can also comprise a nutrient solution or a growth inducer in dried (i.e., dehydrated) or lyophilized form within the active electrode wells 220 and the growth control wells 218, respectively. This can be the case when the inoculum solution 110 comprises the infectious agent 106 diluted in deionized water or a saline solution. For example, the active electrode wells 220 can comprise a dried or lyophilized form of a yeast extract, beef extract, cation-adjusted Mueller Hinton Broth (CAMHB), Mueller Hinton (MH) broth, starch, acid hydrolysate of casein, calcium chloride, magnesium chloride, sodium chloride, blood or lysed blood including lysed horse blood (LHB), CAMHB-LHB, glucose, or a combination thereof.

The inoculum solution 110 can re-hydrate the dried or lyophilized anti-infective 108 when the inoculum solution 110 flows into the plurality of active electrode wells 220. The inoculum solution 110 can be in fluid communication with the pH electrode 130 (including the pH sensitive material), the ORP electrode 132 (including the redox sensitive material), and the solid-state reference electrode 216 when the inoculum solution 110 fills the wells 212. Once the inoculum solution 110 has filled the plurality of wells 212, the excess inoculum solution 110 can flow out of the sample outlet port 210.

The method 200 can further comprise introducing a water immiscible liquid 152 into the sample receiving space 206 through the sample inlet port 208 in step 2B. The water immiscible liquid 152 can be introduced, delivered, or otherwise injected into the sample receiving space 206 using one or more fluid delivery conduits 116.

The water immiscible liquid 152 can seal the plurality of wells 212 comprising the inoculum solution 110 and prevent the anti-infective 108 within the active electrode wells 220 from flowing out of their respective well cavities, thereby affecting the concentration of the anti-infective 108 within the other active electrode wells 220. Scaling the plurality of wells 212 comprising the inoculum solution 110 can also prevent the growth control wells 218 from being contaminated by the anti-infective 108 from the active electrode wells 220. The water immiscible liquid 152 can also prevent contaminants from entering the plurality of wells 212 once the wells 212 are filled with the inoculum solution 110.

The water immiscible liquid 152 can seal the plurality of wells 212 by filling and occupying the shared space 214. The water immiscible liquid 152 can displace any inoculum solution 110 previously within the shared space 214 out of the sample receiving space 206 through the sample outlet port 210 or push the inoculum solution 110 previously within the shared space 214 into the wells 212. In this manner, the water immiscible liquid 152 can ensure the contents within each of the wells 212 do not disturb measurements within neighboring wells 212.

One advantage of adding the water immiscible liquid 152 after the inoculum solution 110 has been introduced into the plurality of wells 212 is that the water immiscible liquid 152 does not significantly displace the inoculum solution 110 in fluid contact with the electrodes (e.g., the pH electrodes 130, the ORP electrodes 132, and the solid-state reference electrodes 216) within the wells 212. One explanation could be that the hydrophilic inoculum solution 110 is drawn more to the metal and metal oxide layers of the pH electrodes 130, the ORP electrodes 132, and the solid-state reference electrodes 216 than the hydrophobic water immiscible liquid 152. As such, the water immiscible liquid 152 acts to seal or cover the entrance or openings to the wells 212 containing the inoculum solution 110.

The water immiscible liquid 152 can be a hydrophobic oil or solvent. In some embodiments, the water immiscible liquid 152 can be silicone oil, a non-polar solvent, or a combination thereof. The water immiscible liquid 152 can be gas permeable and allow oxygen and carbon dioxide to permeate through the water immiscible liquid 152.

The method 200 can also comprise incubating the diagnostic device 202 comprising the inoculum solution 110 and the water immiscible liquid 152 at an elevated temperature for a predetermined time period 154 in step 2C. In some embodiments, the diagnostic device 202 can be incubated by being heated to a temperature of between about 30° C. and about 40° C. (e.g., 35° C.±2° C.).

In these and other embodiments, the diagnostic device 202 can be allowed to incubate at the elevated temperature for between about 15 minutes and 60 minutes. In other embodiments, the diagnostic device 202 can be allowed to incubate at the elevated temperature for between about 60 minutes and 120 minutes. In additional embodiments, the diagnostic device 202 can be allowed to incubate at the elevated temperature for between about 120 minutes and 240 minutes. In further embodiments, the diagnostic device 202 can be allowed to incubate at the elevated temperature for between about 240 minutes and 480 minutes. In certain embodiments, the diagnostic device 202 can be allowed to incubate at the elevated temperature for between about 480 minutes and up to about 48 hours.

The predetermined time period 154 (or the incubation period) can be adjusted based on the type of infectious agent 106 suspected in the inoculum solution 110, such as the type of bacteria or fungus. The predetermined time period 154 can also be adjusted based on the type of anti-infective 108, the mechanism of action of the anti-infective 108, the amount of the inoculum solution 110 introduced into the diagnostic device 202, or a combination thereof. The predetermined time period 154 (or the incubation period) can be start-delayed or a pre-incubation time period can be added before the start of the incubation period. The start-delay or the pre-incubation time period can be added for slower acting drugs or anti-infectives 108 (e.g., beta-lactams). In some embodiments, the start-delay or the pre-incubation time period can be between 10 minutes and 2 hours. In other embodiments, the start-delay or the pre-incubation time period can be as long as needed for the drug or anti-infective 108 to take effect. During the start-delay or pre-incubation time period, readings or measurements from the electrodes would not be used or would not be included as part of any growth curves generated (pH or ORP signals monitored). The start-delay or the pre-incubation time period is particularly useful for instances where higher concentrations of the infectious agent 106 are present in the inoculum solution 110 and where the signal is generated relatively fast in comparison to the mode of action of the drug or anti-infective 108.

The method 200 can further comprise an optional step of identifying a species or other classification type or characteristic of the infectious agent 106 in the inoculum solution 110. In addition to species, the other classification type can comprise a genus, a family, an order, a class, a phylum, a kingdom, and a domain of the infectious agent 106 in the inoculum solution 110.

In some embodiments, identifying the species or other classification type of the infectious agent 106 can involve receiving such information from a user via an input device (e.g., a keyboard or touchscreen) coupled to a computing device 158 of the system 204. In other embodiments, identifying the species or other classification type of the infectious agent 106 can involve receiving such information from another computing device communicatively coupled to the computing device 158 or retrieving such information from a database. The classification-type (e.g., the species, the genus, the family, etc.) or the characteristic of the infectious agent 106 can be stored in a memory of the computing device 158, a computing cloud, or a remote server accessible to the computing device 158 over a network.

In some embodiments, identifying the species of the infectious agent 106 in the inoculum solution 110 can involve determining the species using a biochemical test (e.g., a test for metabolism or a test for specific enzymes), mass spectrometry, genotyping, phenotypic analysis from culture plates, test kits comprising phages, or a combination thereof. In other embodiments, the characteristic of the infectious agent 106 can be a response of the infectious agent 106 to a Gram stain test. For example, the method 200 can comprise performing a Gram stain test and identifying the infectious agent 106 as Gram-positive or Gram-negative bacteria. In certain embodiments, the species of the infectious agent 106 in the inoculum solution 110 can be identified but the particular strain of the infectious agent 106 can be left unknown. As previously discussed, the incubation period can be adjusted based on the species of the infectious agent 106 in the inoculum solution 110.

The method 200 can also comprise monitoring one or more solution characteristics of the inoculum solution 110 within the active electrode wells 220 and the growth control wells 218 over the predetermined time period 154 in step 2D. In some embodiments, monitoring the one or more solution characteristics of the inoculum solution 110 within the active electrode wells 220 and the growth control wells 218 can be done while the diagnostic device 202 is being incubated at the elevated temperature.

The one or more solution characteristics monitored can comprise the pH of the inoculum solution 110, the ORP of the inoculum solution 110, and both the pH and the ORP of the inoculum solution 110. In some embodiments, the one or more solution characteristics can be monitored without or in the absence of any reporter molecules or exogenous reporter molecules added to the inoculum solution 110.

The solution characteristic of the inoculum solution 110 within the active electrode wells 220 and the growth control wells 218 can change as the amount of ions or the amount of electro-active redox species in solution changes due to the energy use, oxygen uptake or release, growth, or metabolism of the infectious agent 106 in the active electrode wells 220 and the growth control wells 218. For example, the amount of electro-active redox species in solution in the active electrode wells 220 and the growth control wells 218 can change because of cellular activity (e.g., microbial aerobic or anaerobic respiration) undertaken by the infectious agents 106 in the active electrode wells 220 and the growth control wells 218. Also, as an example, the amount of $H^+$ ions in the inoculum solution 110 can change as a result of cellular activity undertaken by the infectious agents 106 in solution in the various active electrode wells 220 and the growth control wells 218.

The method 200 can further comprise comparing the one or more solution characteristics of the inoculum solution 110 within the growth control wells 218 with the one or more solution characteristics of the inoculum solution 110 within the various active electrode wells 220 to determine the minimum inhibitory concentration (MIC) of the anti-infective 108 on the infectious agent 106 in step 2E. For example, when the solution characteristic of the inoculum solution 110 monitored is pH, the MIC of the anti-infective 108 on the infectious agent 106 can be determined by comparing the pH of the inoculum solution 110 within the growth control wells 218 with the pH of the inoculum solution 110 within the various active electrode wells 220. As another example, when the solution characteristic of the inoculum solution 110 monitored is the ORP of the solution, the MIC of the anti-infective 108 on the infectious agent 106 can be determined by comparing the ORP of the inoculum solution 110 within the growth control wells 218 with the ORP of the inoculum solution 110 within the various active electrode wells 220. In an additional example, when the solution characteristic of the inoculum solution 110 monitored is both pH and ORP, the MIC of the anti-infective 108 on the infectious agent 106 can be determined by comparing the pH and ORP of the inoculum solution 110 within the growth control wells 218 with the pH and ORP of the inoculum solution 110 within the various active electrode wells 220.

In some embodiments, monitoring the one or more solution characteristics of the inoculum solution 110 within the growth control wells 218 and the one or more solution characteristics of the inoculum solution 110 within the active electrode wells 220 can be done using one or more parameter analyzers 156. The one or more parameter analyzers 156 can be coupled to the pH electrodes 130, the ORP electrodes 132, and the solid-state reference electrodes 216 within the growth control wells 218 and the pH electrodes 130, the ORP electrodes 132, and the solid-state reference electrodes 216 within the active electrode wells 220.

The pH of the inoculum solution 110 can be determined using the parameter analyzer 156 based on a difference between the potential measured at an active electrode (e.g., one of the pH electrodes 130) and the potential measured at a solid-state reference electrode 216. Similarly, the ORP of the inoculum solution 110 can be determined using the parameter analyzer 156 based on a difference between the potential measured at an active electrode (e.g., one of the ORP electrodes 132) and the potential measured at a solid-state reference electrode 216.

In certain embodiments, the one or more parameter analyzers 156 can be or refer to one or more voltmeters, multimeters, or other voltage-measurement apparatus. In some embodiments, the one or more parameter analyzers 156 can be integrated with the diagnostic device 202. For example, the one or more parameter analyzers 156 can comprise one or more chips or circuitry fabricated on the substrate layer 122 of the diagnostic device 202. In other embodiments, the one or more parameter analyzers 156 can be standalone devices such as standalone voltmeters or multimeters. The parameter analyzers 156 can be electrically coupled to the pH electrodes 130, the ORP electrodes 132, and the solid-state reference electrodes 216 via conductive wires, traces, other conductive connections, or a combination thereof.

The parameter analyzer 156 can also be coupled, either directly or communicatively, to a computing device 158. The diagnostic device 202, the one or more parameter analyzers 156 and the computing device 158 can be part of the system 204. In some embodiments, the parameter analyzer 156 and the computing device 158 can be integrated into one device or apparatus. In other embodiments, the parameter analyzer 156 can be integrated with the diagnostic device 202 (e.g., fabricated on a surface or substrate layer 122 of the diagnostic device 202) and the entire diagnostic device 202 can be detachably coupled via one or more hardware interfaces or connections to the computing device 158. In these embodiments, the computing device 158 can act as a reader of the diagnostic device 202. For example, the diagnostic device 202 can be configured as a cartridge, a test strip, a microfluidic chip or device, a lab-on-a-chip (LOC) device, a micro-electro-mechanical system (MEMS) device, a portion therein, or a combination thereof.

In some embodiments, the computing device 158 can be or refer to a desktop computer, a laptop computer, a tablet device, a mobile device, a handheld device, or a combination thereof. In other embodiments, the computing device 158 can be or refer to a server, a computing node, a cloud computing resource, or a combination thereof. The computing device 158 can comprise a display such as a desktop monitor, a laptop monitor, a tablet display, a mobile display, or a combination thereof. In additional embodiments, the computing device 158 can be any device comprising one or more processors, a memory, a display or display interface, and a hardware interface configured to couple and communicate with the parameter analyzer 156.

The parameter analyzer 156, the computing device 158, or a combination thereof can monitor the one or more solution characteristics of the inoculum solution 110 within the growth control wells 218 and the one or more solution characteristics of the active electrode wells 220 by generating one or more infectious agent growth curves 160 tracking the change in the solution characteristics. For example, the infectious agent growth curves 160 can be bacterial growth curves or fungi growth curves. The infectious agent growth curves 160 can track the change in pH of the inoculum solution 110, the change in the ORP of the inoculum solution 110, or a combination thereof over time.

As previously discussed, the method 100 can further comprise comparing the one or more solution characteristics of the inoculum solution 110 within the growth control wells 218 with the one or more solution characteristics of the inoculum solution 110 within the active electrode wells 220 to determine the minimum inhibitory concentration (MIC) of the anti-infective 108 on the infectious agent 106. Comparing the one or more solution characteristics of the inoculum solution 110 within the growth control wells 218 with the one or more solution characteristics of the inoculum solution 110 within the active electrode wells 220 can be done using the parameter analyzer 156, the computing device 158 coupled to the parameter analyzer 156, or a combination thereof.

In some embodiments, the computing device 158, the parameter analyzer 156, or a combination thereof can compare the infectious agent growth curves 160 generated from the monitored inoculum solutions 110 within the growth control wells 218 with the infectious agent growth curves 160 generated from the monitored inoculum solutions 110 within the active electrode wells 220. As previously discussed, the active electrode wells 220 can comprise the anti-infective 108 at differing concentrations. For example, the infectious agent growth curves 160 can be compared based on at least one of a (1) time to a pH threshold, (2) a length of an initial lag time, (3) a slope of an exponential phase of the growth curve, (4) a time to a stationary phase of the growth curve, (5) a total curve amplitude, and (6) an area under the curve.

For example, as shown in FIG. 2, the anti-infective 108 assayed can be Ciprofloxacin and the active electrode wells 220 can comprise Ciprofloxacin at concentrations of 1 μg/mL, 2 μg/mL, 4 μg/mL, 8 μg/mL, and 16 μg/mL. In this example, the inoculum solution 110 can be determined to comprise the bacteria *Escherichia coli* (*E. coli*). Bacterial growth curves can be generated from the change in solution characteristics of the inoculum solution 110 present in each of the growth control wells 218 and the active electrode wells 220. The bacterial growth curves generated can include pH growth curves, ORP growth curves, or a combination thereof.

The various bacterial growth curves generated from measurements of the inoculum solutions 110 within the active electrode wells 220 can then be compared to the bacterial growth curves generated from measurements of the inoculum solutions 110 within the growth control wells 218. The computing device 158, the parameter analyzer 156, or a combination thereof can compare the bacterial growth curves based on one or more of the following curve attributes: (1) time to a pH threshold, (2) a length of an initial lag time, (3) a slope of an exponential phases of the growth curve, (4) a time to a stationary phase of the growth curve, (5) a total curve amplitude, and (6) an area under the curve. If the parameter analyzer 156, the computing device 158, or a combination thereof determined that the bacterial growth curves of active electrode wells 220 comprising a Ciprofloxacin concentration of less than or equal to 8 μg/mL did not differ significantly (i.e., no statistically significant difference) from the bacterial growth curves of the growth control wells 218 then this particular strain of *E. coli* in the inoculum solution 110 would be considered resistant to Ciprofloxacin at such concentrations. Moreover, if the parameter analyzer 156, the computing device 158, or a combination thereof determined that the bacterial growth curves of active electrode wells 220 comprising a Ciprofloxacin concentration of 16 μg/mL did differ significantly (i.e., exhibits a statistically significant difference) from the bacterial growth curves of the growth control wells 218, then this particular strain of *E. coli* in the inoculum solution 110 would be considered susceptible to Ciprofloxacin at such concentrations and above. In this case, the MIC of Ciprofloxacin on this particular strain of *E. coli* in the inoculum solution 110 would be determined to be 16 μg/mL.

In some embodiments, one or more of the aforementioned steps of the method 200 can be stored as machine-executable instructions or logical commands in a non-transitory machine-readable medium (e.g., a memory or storage unit) of the parameter analyzer 156, the computing device 158, or another device communicatively or electrically coupled to the parameter analyzer 156 or the computing device 158. Any of the parameter analyzer 156, the computing device 158, or another device coupled to the parameter analyzer 156 or the computing device 158 can comprise one or more processors or controllers configured to execute the aforementioned instructions or logical commands.

The steps depicted in FIG. 2 do not require the particular order shown to achieve the desired result. Moreover, certain steps or processes may be omitted or occur in parallel in order to achieve the desired result. In addition, any of the systems or devices disclosed herein can be used in lieu of devices or systems shown in the steps of FIG. 2.

FIGS. 3A-3C illustrate cross-sectional side views of multiple embodiments of a sample receiving space 300 of a diagnostic device 302 for determining the susceptibility of the infectious agent 106 to the anti-infective 108. The diagnostic device 302 shown in FIGS. 3A-3C can be embodiments of the diagnostic device 102 shown in FIG. 1 or embodiments of the diagnostic device 202 shown in FIG. 2. For example, the sample receiving space 300 can be a representation of the sample receiving space 112 of FIG. 1 or the sample receiving space 206 of FIG. 2. The sample receiving space 300 can be enclosed by a device housing 304 comprising a housing top layer 306, housing lateral sides 308, and a housing base layer 310.

In some embodiments, the device housing 304 (including the housing top layer 306, the housing lateral sides 308, the housing base layer 310, portions therein, or a combination thereof) can be made of an inert or non-conductive material. For example, the device housing 304 can comprise or be made in part of a polymeric material such as polyvinyl chloride (PVC), poly(methyl methacrylate) (PMMA), polydimethylsiloxane (PDMS), a ceramic, glass, or a combination thereof. In these and other embodiments, the housing base layer 310 can comprise or be made in part of a substrate layer (e.g., the substrate layer 122) or a semiconductor layer. In these embodiments, the electrodes (e.g., the pH electrodes 130, the ORP electrodes 132, the solid-state reference electrodes 216, or a combination thereof) can be fabricated on the housing base layer 310 or extend from the housing base layer 310 (as shown in FIGS. 3A and 3B).

As shown in FIG. 3C, the housing top layer 306 can also comprise or be made in part of a substrate layer (e.g., the substrate layer 122) or a semiconductor layer. In this embodiment, the electrodes (e.g., the pH electrodes 130, the ORP electrodes 132, the solid-state reference electrodes 216, or a combination thereof) can be fabricated on the housing top layer 306 or extend from the housing top layer 306 into the sample receiving space 300. In some embodiments, the housing top layer 306, the housing base layer 310, or a combination thereof can comprise or be made in part of a transparent material or a translucent material such that a user can see the inoculum solution 110 entering and filling up the sample receiving space 300. In other embodiments, the housing top layer 306, the housing base layer 310, or a combination thereof can comprise or be made in part of an opaque material such that a user cannot see the inoculum solution 110 entering and filling up the sample receiving space 300.

The diagnostic device 300 (which can be a side cross-sectional view of any of the diagnostic device 102 shown in FIG. 1 or the diagnostic device 202 shown in FIG. 2) can comprise a sample inlet port 312 and a sample outlet port 314. The sample inlet port 312 can be or refer to any of the sample inlet port 114 shown in FIG. 1 or the sample inlet port 208 shown in FIG. 2. The sample outlet port 314 can be or refer to any of the sample outlet port 118 shown in FIG. 1 or the sample outlet port 210 shown in FIG. 2.

The sample inlet port 312 can comprise an inlet port diameter 316. The inlet port diameter 316 can be between about 0.5 mm to about 1.0 mm. The outlet port diameter 318 can be between about 0.5 mm to about 1.0 mm. The sample inlet port 312 can be located or positioned at one end of the sample receiving space 300 and the sample outlet port 314 can be located or positioned at another end of the sample receiving space 300. As shown in FIGS. 3A and 3B, in some embodiments, the sample inlet port 312 and the sample outlet port 314 can be defined on the housing top layer 306. In other embodiments such as those shown in FIG. 3C, the sample inlet port 312 and the sample outlet port 314 can be defined on the housing base layer 310. In additional embodiments contemplated by this disclosure, the sample inlet port 312 and the sample outlet port 314 can also be defined or positioned along a surface of the housing lateral sides 308. A valve (e.g., a one-way valve), gate, or flow regulator can be positioned within the sample inlet port 312 or the sample outlet port 314 to prevent the inoculum solution 110 from inadvertently flowing out of the sample inlet port 312 or inadvertently flowing back into the sample outlet port 314.

The sample receiving space 300 can also comprise a plurality of wells 320. The wells 320 shown in FIG. 3 can be or refer to any of the wells 120 of FIG. 1 or the wells 212 of FIG. 2.

The wells 300 can be substantially cylindrical-shaped, bowl-shaped, or hemispherical indentations, divots, depressions, or cavities defined along the housing base layer 310 or the housing top layer 306. In other embodiments, the wells 300 can be shaped substantially as an upside-down conic, a frustoconic or upside-down frustoconic, a partial ovoid, or a combination thereof. In additional embodiments, the wells 300 can be substantially cuboid-shaped.

Each of the wells 320 can have a well height 322 and a well diameter 324. When the wells 320 are substantially cylindrical-shaped, the well height 322 can be a height dimension of the cylinder and the well diameter 324 can be a diameter of the cylinder. In other embodiments, when the wells 320 are substantially dome-shaped, bowl-shaped, or hemispherical, the well height 322 can be a maximum well depth and the well diameter 324 can be a diameter of the well opening (i.e., the base of the dome, bowl, or hemisphere).

The wells 320 can be configured such that an aspect ratio of the well height 322 to the well diameter 324 is between about 1:1 to about 1:2. In some embodiments, the well height 322 can be between about 400 μm and 600 μm, the well diameter 324 can be between about 400 μm and 1.2 mm. As a more specific example, each of the wells 320 can have a well height 322 of about 500 μm and a well diameter 324 of about 700 μm. One discovery made by the applicant is that wells (e.g., the wells 120, the wells 212, or a combination thereof) having a well height 322 to well diameter 324 ratio of between about 1:1 to about 1:2 were more suited to the operation of the diagnostic device (e.g., the diagnostic device 102, the diagnostic device 202, or a combination thereof) than other well dimensions.

Each of the wells 320 can also have a well volume. The well volume can be an amount of the inoculum solution 110 or another sample solution held or contained by the well 320. In some embodiments, the well volume can be between about 0.8 μL to about 1.2 μL. More specifically, the well volume can be about 1.0 μL. In some embodiments, the size of the well and the well volume can be configured such that each well 320 comprised approximately 100 colony-forming units (CFU) of the infectious agent 106.

The plurality of wells 320 can also be separated by one or more well walls 326. The well walls 326 can be dividers, partitions, or other raised surfaces configured to divide one well 320 from another. In some embodiments, the well walls 326 can be made of an inert or non-conductive material. For example, the well walls 326 can comprise or be made in part of a polymeric material such as polyvinyl chloride (PVC), poly(methyl methacrylate) (PMMA), polydimethylsiloxane (PDMS), a ceramic, glass, or a combination thereof. The well walls 326 can separate active electrode wells 328 from growth control wells 330. Moreover, the well walls 326 can also separate each of the active electrode wells 328 from other active electrode wells 328.

In some embodiments, one or more well walls 326 can also separate electrodes 332 within each of the wells 320. The electrodes 332 shown in FIGS. 3A-3C can be or refer to any of the pH electrodes 130, the ORP electrodes 132, or a combination thereof shown in FIGS. 1 and 2. In other embodiments, multiple electrodes 332 can be positioned or located within one well 320 without the electrodes 332 being separated by well walls 326 (see, e.g., FIG. 2 and FIG. 4B).

As shown in FIGS. 3A-3C, the active electrode wells 328 can comprise the anti-infective 108 in at least one of a dried form and a lyophilized form. For example, the anti-infective 108 can coat, cover, or be otherwise deposited on a surface of the electrodes 332 within the active electrode wells 328. The amount or concentration of the anti-infective 108 can vary between active electrode wells 328. As a more specific example, the anti-infective 108 can be injected or delivered into each of the active electrode wells 328 initially in liquid form and allowed to dry over time (e.g., between about 20 hours to 30 hours or more). In other embodiments contemplated by this disclosure, the anti-infective 108 can cover, coat, or otherwise be deposited on a surface in the vicinity of the electrodes 332 but not directly on the electrodes 332. In these embodiments, the anti-infective 108 can cover, coat, or otherwise be deposited on a well wall 326, the housing base layer 310, the housing top layer 306, or a combination thereof.

In additional embodiments, the active electrode wells 328 and the growth control wells 330 can comprise a nutrient medium or growth inducer in at least one of a dried form and a lyophilized form. For example, the dried or lyophilized nutrient medium or growth induce can coat, cover, or be otherwise deposited on a surface of the electrodes 332 within the active electrode wells 328 and the growth control wells 330. This can be the case when the inoculum solution 110 comprises the infectious agent 106 suspended or diluted in deionized water or a saline solution.

As a more specific example, the nutrient medium or growth inducer can be injected or delivered into each of the active electrode wells 328 and the growth control wells 330 initially in liquid form and allowed to dry over time (e.g., between about 20 hours to 30 hours or more). In other embodiments contemplated by this disclosure, the dried or lyophilized nutrient medium or growth inducer can cover, coat, or otherwise be deposited on a surface in the vicinity of the electrodes 332 but not directly on the electrodes 332. In these embodiments, the nutrient medium or growth inducer can cover, coat, or otherwise be deposited on a well wall 326, the housing base layer 310, the housing top layer 306, or a combination thereof.

FIGS. 3A-3C also illustrate that the sample receiving space 300 can comprise a shared space 334. The shared space 334 can be a portion of the sample receiving space 300 in fluid communication with all of the wells 320. For example, the shared space 334 can be the portion of the sample receiving space 300 above the wells 320 when the wells 320 are defined or positioned along the housing base layer 310. In other example embodiments, the shared space 334 can be the portion of the sample receiving space 300 below the wells 320 when the wells 320 are defined or positioned along the housing top layer 306. In all such embodiments, the shared space 334 can be in fluid communication with the sample inlet port 312 and the sample outlet port 314.

The shared space 334 can have a shared space height 336 and a shared space volume. In some embodiments, the shared space height 336 can be about 80 μm to about 120 μm. In these and other embodiments, the shared space volume can be about 80 μL to about 120 μL. Although FIGS. 3A-3C show the diagnostic device 302 comprising only four wells 320, it is contemplated by this disclosure and it should be understand by one of ordinary skill in the art that the diagnostic device 302 (e.g., the diagnostic device 102 of FIG. 1 and the diagnostic device 202 of FIG. 2) can comprise between 100-200 wells 320.

As shown in FIGS. 3A-3C, the inoculum solution 110 can be injected, delivered, or otherwise introduced into the sample receiving space 300 (which can refer to either the sample receiving space 112 or the sample receiving space 206) through the sample inlet port 312. The inoculum solution 110 can fill the sample receiving space 300 including the wells 320 prior to flowing out of the sample receiving space 300 through the sample outlet port 314. A next step in the operation of the diagnostic device 302 (which can refer to either the diagnostic device 102 or the diagnostic device 202) can comprise injecting, delivering, or otherwise introducing a water immiscible liquid 152 into the sample receiving space 300 through the sample inlet port 312. The water immiscible liquid 152 can be introduced, delivered, or otherwise injected into the sample receiving space 300 using one or more fluid delivery conduits 116.

The water immiscible liquid 152 can seal the plurality of wells 320 (which can refer to either the wells 120 or the wells 212) comprising the inoculum solution 110 and prevent the anti-infective 108 within the active electrode wells 328 from flowing out of their respective well cavities, thereby affecting the concentration of the anti-infective 108 within the other active electrode wells 328. Sealing the plurality of wells 320 comprising the inoculum solution 110 can also prevent the growth control wells 330 (which can refer to either the growth control wells 134 or the growth control wells 218) from being contaminated by the anti-infective 108 from the active electrode wells 328. The water immiscible liquid 152 can also prevent contaminants from entering the plurality of wells 320 once the wells 320 are filled with the inoculum solution 110.

The water immiscible liquid 152 can seal the plurality of wells 320 by filling and occupying the shared space 334. The water immiscible liquid 152 can displace any inoculum solution 110 previously within the shared space 334 out of the sample receiving space 300 through the sample outlet port 314 or push the inoculum solution 110 previously within the shared space 334 into the wells 320. In this manner, the water immiscible liquid 152 can ensure the contents within each of the wells 320 do not disturb measurements within neighboring wells 320.

One advantage of adding the water immiscible liquid 152 after the inoculum solution 110 has been introduced into the plurality of wells 320 is that the water immiscible liquid 152 does not significantly displace the inoculum solution 110 in fluid contact with the electrodes 332 (which can refer to the pH electrodes 130 or the ORP electrodes 132) within the wells 320. One explanation could be that the hydrophilic inoculum solution 110 is drawn more to the metal or metal oxide layers of the electrodes 332 than the hydrophobic water immiscible liquid 152. As such, the water immiscible liquid 152 acts to seal or cover the entrance or openings to the wells 320 containing the inoculum solution 110. Another advantage of the water immiscible liquid 152 is that it causes minimal disruption to the functioning of the electrodes 332.

The water immiscible liquid 152 can be a hydrophobic oil or solvent. In some embodiments, the water immiscible liquid 152 can be silicone oil, a non-polar solvent, or a combination thereof. The water immiscible liquid 152 can be gas permeable and allow oxygen and carbon dioxide to permeate through the water immiscible liquid 152.

Figure 4A:
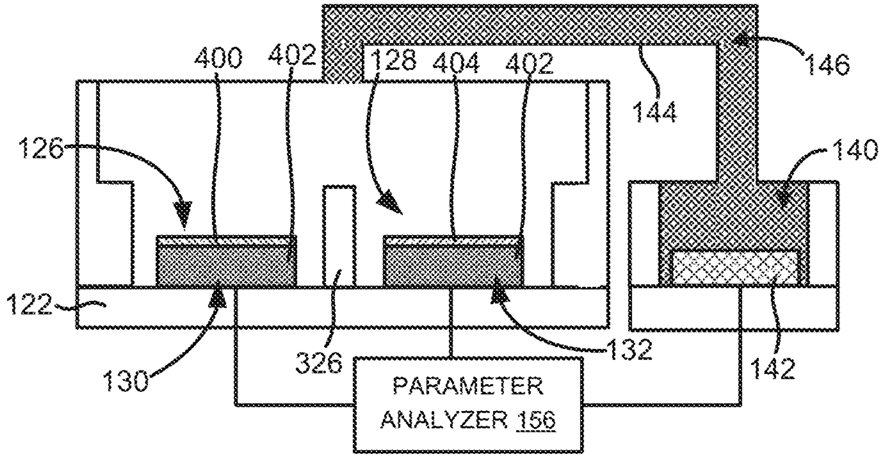
FIG. 4A illustrates a schematic of an embodiment of a pH electrode well and an ORP electrode well in fluid communication with a reference electrode well.

FIG. 4A illustrates a schematic of an embodiment of a pH electrode well 126 and an ORP electrode well 128 in fluid communication with a reference electrode well 140. The pH electrode well 126 and the ORP electrode well 128 depicted in FIG. 4A can be or refer to any of the growth control wells 134 or any of the active electrode wells 136 shown in FIG. 1. Although not shown in FIG. 4A, when the pH electrode well 126 and the ORP electrode well 128 are active electrode wells 136, at least a portion of the pH electrode 130 and at least a portion of the ORP electrode 132 can be covered by the anti-infective 108.

The pH electrode well 126 can comprise a pH electrode 130 comprising a pH sensitive layer 400 and a conductor layer 402. The pH sensitive layer 400 can be coupled to, deposited on, or otherwise affixed to the conductor layer 402. The pH sensitive layer 400 can be the layer or surface of the pH electrode 130 in fluid communication with the inoculum solution 110 when the inoculum solution 110 is introduced or delivered into the pH electrode well 126.

The pH sensitive layer 400 can comprise or be made in part of a pH sensitive material. In some embodiments, the pH sensitive material can comprise or be made in part of silicon dioxide ($SiO_2$), aluminum oxide ($Al_2O_3$), titanium dioxide ($TiO_2$), tantalum pentoxide ($Ta_2O_5$), hafnium dioxide ($HfO_2$), or a combination thereof. The pH electrode 130 can be positioned at the bottom of the pH electrode well 126 (such as on the substrate layer 122 or a housing base layer). In other embodiments, the pH electrode 130 can be positioned at the top of the pH electrode well 126 (such as on the substrate layer 122 or a housing top layer).

The pH sensitive layer 400 can be configured to interact with ions, analytes, or other molecules or by products in the inoculum solution 110. For example, the pH sensitive layer 400 can comprise hydroxyl groups which can interact with hydrogen ions ($H^+$) in the inoculum solution 110.

The conductor layer 402 can comprise or be made in part of a metal, a semiconducting material, a metal/metal-salt, or a combination thereof. For example, the conductor layer 402 can comprise or be made in part of silicon, gold, silver, aluminum, platinum, or a composite thereof. The conductor layer 402 can also comprise or be made in part of an organic semiconductor, a carbon nanotube, graphene, an organic conductor such as those derived from polyacetylene, polyaniline, Quinacridone, Poly(3,4-ethylenedioxythiophene) or PEDOT, PEDOT: polystyrene sulfonate (PSS), or a combination thereof. The conductor layer 402 can also comprise or be made in part of any conductive material which allows an electrical property change to be measured (e.g., a voltage change, a capacitance change, a conductance change, and/or a current change) through the conductor layer 402. The conductor layer 402 can also refer to multiple conductive layers such as a stack of metallic layers. For example, the metallic layers can comprise gold layers, silver layers, platinum layers, or a combination thereof.

The ORP electrode well 128 can comprise an ORP electrode 132 comprising a redox sensitive layer 404 and the conductor layer 402. The redox sensitive layer 404 can be coupled to, deposited on, or otherwise affixed to the conductor layer 402. The redox sensitive layer 404 can be the layer or surface of the ORP electrode 132 in fluid communication with the inoculum solution 110 when the inoculum solution 110 is introduced or delivered into the ORP electrode well 128.

The redox sensitive layer 404 can comprise or be made in part of a redox sensitive material. In some embodiments, the redox sensitive material can comprise or be made in part of $SiO_2$, $Al_2O_3$, $TiO_2$, $Ta_2O_5$, $HfO_2$, iridium dioxide ($IrO_2$), ruthenium dioxide ($RuO_2$), zirconium dioxide ($ZrO_2$), or a combination thereof. The ORP electrode 132 can be at the bottom of the ORP electrode well 128 (such as on the substrate layer 122 or a housing base layer).

The pH sensitive layer 400, the redox sensitive layer 404, or a combination thereof can also be covered one or more functionalization layers. The functionalization layers can comprise silanes, DNA, proteins, antibodies, self-assembled mono layers (SAMs), buffered hydrogels, parylene, or another biochemically active material.

As shown in the example embodiment of FIG. 4A, the pH electrode well 126 can be a separate well from the ORP electrode well 128 and the pH electrode 130 can be separated from the ORP electrode 132 by one or more well walls 326. Each of the pH electrode wells 126 and each of the ORP electrode wells 128 can be sized according to the well dimensions and well volumes discussed with respect to wells 320 of FIGS. 3A-3C.

Figure 4B:
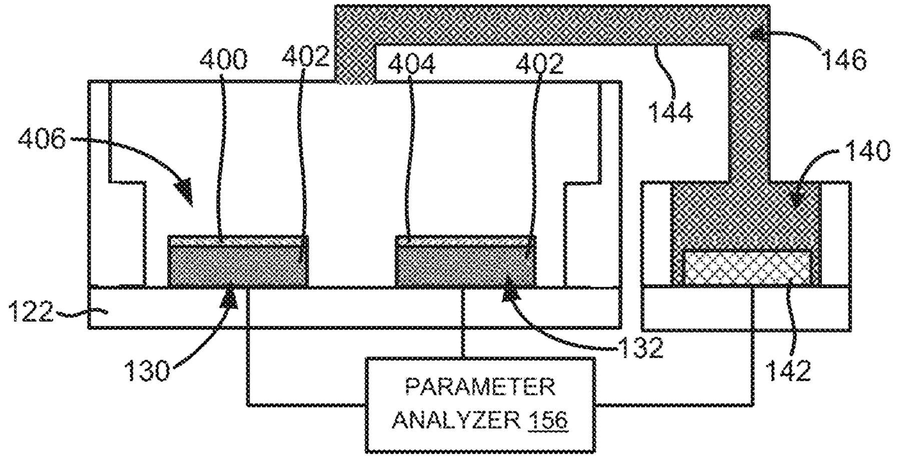
FIG. 4B illustrates a schematic of another embodiment of a single well comprising both a pH electrode and an ORP electrode in fluid communication with a reference electrode well.

FIG. 4B illustrates another embodiment of a singular well 406 comprising both a pH electrode 130 and an ORP electrode 132. In this embodiment, the pH electrode 130 and the ORP electrode 132 are not separated by well walls 326.

As shown in FIGS. 4A and 4B, the pH electrode well 126 and the ORP electrode well 128 can be in fluid communication with a reference electrode well 140 via a connecting conduit 144. The reference electrode well 140 can be a separate well connected to the pH electrode well 126 and the ORP electrode well 128 by the connecting conduit 144.

As shown in FIG. 4A, the connecting conduit 144 can connect the reference electrode well 140 to a shared space above the pH electrode well 126 and the ORP electrode 132. As shown in FIG. 4B, the connecting conduit 144 can also connect the reference electrode well 140 to a singular well 406 comprising both the pH electrode 130 and the ORP electrode 132. In additional embodiments contemplated by this disclosure, each of the pH electrode wells 126 can be connected to a reference electrode well 140 by a connecting conduit 144 and each of the ORP electrode wells 128 can be connected to a reference electrode well 140 by another connecting conduit 144.

The connecting conduit 144 can refer to a channel, passageway, or capillary. For example, the connecting conduit 144 can be a microfluidic channel. Each of the connecting conduits 144 can be at least partially filled by a reference buffer 146. The reference buffer 146 can fill the plurality of reference electrode wells 140. The reference buffer 146 can act as a salt bridge or liquid bridge connecting the reference buffer 146 within the reference electrode wells 140 to the inoculum solution 110 within the pH electrode wells 126, the ORP electrode wells 128, or a combination thereof. The reference buffer 146 can allow the reference electrodes 142 to be in ion exchange contact with the inoculum solution 110 within the pH electrode wells 126, the ORP electrode wells 128, or a combination thereof.

In some embodiments, the reference buffer 146 can be or comprise an aqueous reference buffer solution. In some embodiments, the aqueous reference buffer solution can be an aqueous redox buffer solution comprising deionized water (e.g., about 95%-99%), potassium hexacyanoferrate (III) (e.g., about 0.1% to 0.9%), potassium hexacyanoferrate (II) (e.g., about 0.1% to 0.9%), potassium dihydrogen phosphate (e.g., less than about 0.5%), and disodium hydrogen phosphate (less than about 0.5%). As a more specific example, the aqueous reference buffer solution can be a 220 mV/pH 7 redox buffer solution (Product Code 51350060) provided by Mettler-Toledo AG.

In other embodiments, the aqueous reference buffer solution can be or comprise a redox buffer solution comprising 3M KCl. As a more specific example, the aqueous reference buffer solution can be a 3M KCl redox buffer solution (Material No. 63056165) provided by Mettler-Toledo AG.

In other embodiments, the reference buffer 146 can be a reference buffer gel. The reference buffer gel can comprise the aqueous reference buffer solution and a thickening agent. In some embodiments, the thickening agent can be agar powder. In other embodiments, the thickening agent can comprise a polysaccharide or polysaccharide powder. As a more specific example, the agar powder used can be a commercially available agar powder such as agar powder provided by Sigma-Aldrich, Inc. (e.g., Sigma-Aldrich™ Agar Powder 05040) or Thermo Fisher Scientific Inc. (e.g., Fisher Scientific™ Agar Powder, Catalog No. S14153).

In one embodiment, the reference buffer gel can comprise the thickening agent at a concentration of about 1% (w/v %, g/mL). In another embodiment, the reference buffer gel can comprise the thickening agent at a concentration of about 5% (w/v %, g/mL). In some embodiments, the reference buffer gel can comprise the thickening agent at a concentration of between about 1% (w/v %, g/mL) and 5% (w/v %, g/mL). In other embodiments, the reference buffer gel can comprise the thickening agent at a concentration of between about 5% (w/v %, g/mL) and 10% (w/v %, g/mL).

The reference buffer gel can be made by heating the aqueous reference buffer solution above the boiling point of the aqueous reference buffer solution and stirring the thickening agent into the heated aqueous reference buffer solution. Once the thickening agent (e.g., the agar powder) is completely dissolved in the heated aqueous reference buffer solution, the hot gel slurry can be introduced into the buffer inlet port 148 via the buffer inlet port 148. The hot gel slurry can fill or otherwise occupy the buffer receiving space 138 including the reference electrode wells 140. The hot gel slurry can also fill or otherwise occupy at least part of the connecting conduits 144. The hot gel slurry can be allowed to cool to room temperature and solidify at room temperature. Once the hot gel slurry is solidified, the reference buffer gel can fill or otherwise occupy the reference electrode wells 140 and at least part of the connecting conduits 144.

The reference electrode well 140 can comprise a reference electrode 142. In some embodiments, the reference electrode 142 can be or comprise a silver/silver chloride (Ag/AgCl) electrode. In other embodiments, the reference electrode 142 can be or comprise a saturated calomel reference electrode (SCE) or a copper-copper (II) sulfate electrode (CSE). In other embodiments, the reference electrode 142 can be a pseudo-reference electrode comprising or made in part of platinum, silver, gold, stainless steel, or a combination thereof. In additional embodiments, the reference electrode 142 can also comprise or be made in part of a metal oxide or semiconductor oxide material or a conductive polymer electrode such as polypyrrole, polyaniline, polyacetylene, or a combination thereof.

When the reference electrode well 140 is filled by the reference buffer 146 (such as the reference buffer gel), at least part of the reference electrode 142 (e.g., the tip or a segment of the reference electrode 142) can be in fluid communication with the reference buffer 146. For example, when the reference buffer 146 is the reference buffer gel, at least part of the reference electrode 142 can pierce through and remain within the reference buffer gel.

The pH electrode 130, the ORP electrode 132, and the reference electrode 142 can be coupled by conductive connections or traces to the parameter analyzer 156. In some embodiments, the conductive connections or traces can comprise copper wires or traces, electro-deposited copper, rolled annealed copper, high-ductility electro-deposited copper, or a combination thereof. In other embodiments, the conductive connections can be made in part of silver or nickel. For example, the parameter analyzer 156 can be coupled to the reference electrode 142 and the conductor layers 402 of the pH electrode 130 and the ORP electrode 132.

As shown in FIGS. 4A and 4B, the pH electrode 130 and the ORP electrode 132 can share the same reference electrode 142. In other embodiments contemplated by this disclosure, the pH electrode 130 and the ORP electrode 132 can each be coupled to its own reference electrode 142. The reference electrode 142 can have a stable or well-known internal voltage and can also act as a differential noise filter for removing electrical noise from measurements taken by the parameter analyzer 156.

In some embodiments, the parameter analyzer 156 can be or comprise a high-impedance voltmeter, amplifier, source-meter, or multi-meter. The parameter analyzer 156 can also be used to apply a voltage or current to the reference electrode 142, the pH electrode 130, the ORP electrode, or a combination thereof.

The parameter analyzer 156 can determine the pH of the inoculum solution 110 by measuring a relative change in an equilibrium potential at an interface between the pH sensitive layer 400 of the pH electrode 130 and the inoculum solution 110 containing the ions, analytes, or other molecules. In other embodiments, the parameter analyzer 156 can also measure a relative change in the equilibrium potential at an interface between the conductor layer 402 below the pH sensitive layer 400 and the inoculum solution 110. The solution characteristic of the inoculum solution 110 can change as the amount of ions, analytes, or other molecules changes due to the energy use, oxygen uptake or release, growth, or metabolism of the infectious agents 106 in solution. For example, the amount of hydrogen ions ($H^+$) in the inoculum solution 110 can change as a result of cellular activity undertaken by the infectious agents 106 in solution. The change in the equilibrium potential can be measured with respect to the reference electrode 142. The parameter analyzer 156 (or the computing device 158 coupled to the parameter analyzer 156) can determine the pH of the inoculum solution 110 by measuring the change in the equilibrium potential at the interface between the pH sensitive layer 400 and the inoculum solution 110 with respect to the reference electrode 142.

The parameter analyzer 156 can determine the ORP of the inoculum solution 110 by measuring a relative change in an equilibrium potential at an interface between the redox sensitive layer 404 of the ORP electrode 132 and the inoculum solution 110 containing the electro-active redox species. In other embodiments, the parameter analyzer 156 can also measure a relative change in the equilibrium potential at an interface between the conductor layer 402 below the redox sensitive layer 404 and the inoculum solution 110. The solution characteristic of the inoculum solution 110 can change as the amount of electro-active redox species changes due to the energy use, oxygen uptake or release, growth, or metabolism of the infectious agents 106 in solution. For example, the amount of electro-active redox species in the inoculum solution 110 can change as a result of cellular activity undertaken by the infectious agents 106 in solution. As a more specific example, the amount of electron donors (e.g., the amount of energy carriers such as nicotinamide adenine dinucleotide (NADH) and flavin adenine dinucleotide ($FADH_2$)) in the inoculum solution 110 can change due to the growth or lack thereof of the infectious agents 106 in solution. Also, as another more specific example, the amount of oxygen depleted in the inoculum solution 110 can change due to the growth or lack thereof of the infectious agents 106 in solution. The change in the equilibrium potential can be measured with respect to the reference electrode 142. The parameter analyzer 156 (or the computing device 158 coupled to the parameter analyzer 156) can determine the ORP of the inoculum solution 110 by measuring the change in the equilibrium potential at the interface between the redox sensitive layer 404 and the inoculum solution 110 with respect to the reference electrode 142.

Figure 4C:
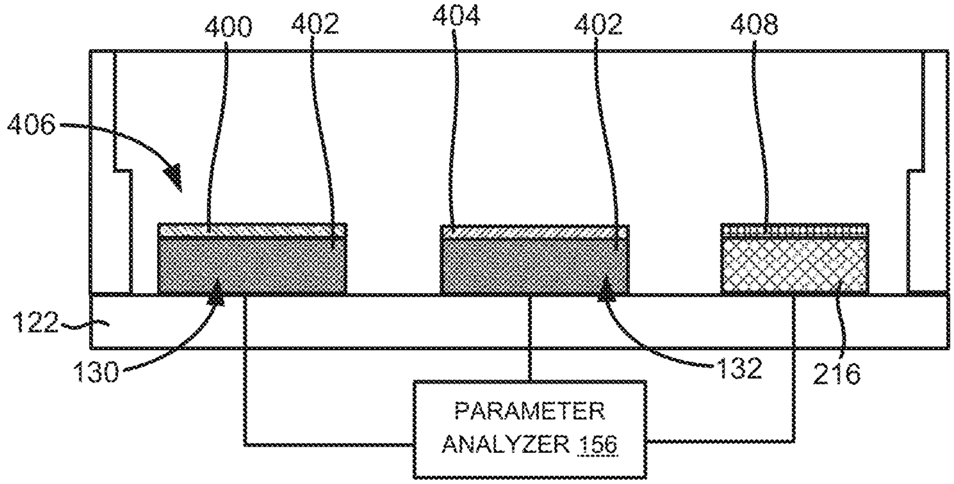
FIG. 4C illustrates a schematic of another embodiment of a well comprising a pH electrode, an ORP electrode, and a solid-state reference electrode.

FIG. 4C illustrates a schematic of a singular well 406 comprising a pH electrode 130, an ORP electrode 132, and a solid-state reference electrode 216. The singular well 406 shown in FIG. 4C can be or refer to any of the wells 212 shown in FIG. 2.

The pH electrode 130 and the ORP electrode 132 of FIG. 4C can be the same pH electrode 130 and the same ORP electrode 132 shown in FIGS. 4A and 4B. For example, the pH electrode 130 can comprise pH sensitive layer 400 coupled to or deposited on a conductor layer 402. Moreover, the ORP electrode 132 can comprise a redox sensitive layer 404 coupled to or deposited on the conductor layer 402.

The pH electrode 130, ORP electrode 132, and the solid-state reference electrode 216 can be separated from one another by a gap or separation distance within the singular well 406. Although FIG. 4C does not show the pH electrode 130, ORP electrode 132, and the solid-state reference electrode 216 being separated by well walls 326, it is contemplated by this disclosure and it should be understood by one of ordinary skill in the art that well walls 326 could separate any of the electrodes shown in FIG. 4C.

The inoculum solution 110 can be in fluid communication or fluid contact with the pH sensitive layer 400 of the pH electrode 130, the redox sensitive layer 404 of the ORP electrode 132, and the solid-state reference electrode 216 when introduced into the well 406.

The solid-state reference electrode 216 can operate similar to the reference electrode 142 and provide the same functionality as the reference electrode 142. In some embodiments, the solid-state reference electrode 216 can comprise or be a silver/silver chloride (Ag/AgCl) electrode. In other embodiments, the solid-state reference electrode 216 can be or comprise a saturated calomel reference electrode (SCE) or a copper-copper (II) sulfate electrode (CSE). In other embodiments, the solid-state reference electrode 216 can be made in part of platinum, silver, gold, stainless steel, or a combination thereof. The pH electrode 130 and the ORP electrode 132 can share the same solid-state reference electrode 216.

A passivation layer 408 can be disposed on or cover the solid-state reference electrode 216. The passivation layer can be configured to prevent the solid-state reference electrode 216 from interacting with redox-active species, hydrogen ions, analytes, or other ions and molecules in the inoculum solution 110. For example, the passivation layer can be a pH-insensitive or redox-insensitive layer.

In some embodiments, the passivation layer 408 can comprise potassium chloride (KCl) electrolyte gel or solution. In these and other embodiments, the passivation layer 408 can comprise a polymeric coating or covering such as a polyvinyl chloride (PVC) coating, a perfluoro-sulfonated ionomer membrane (e.g., a Nafion® membrane provided by E.I. du Pont de Nemours and Company), or a combination thereof. The solid-state reference electrode 216 can also be a reference electrode comprising a miniaturized cell that stabilizes a small internal potential like a calomel electrode.

The solid-state reference electrode 216 can miniaturize and simplify the diagnostic device (e.g., the diagnostic device 102 or the diagnostic device 202). The well design shown in FIG. 4C can also do away with having to add the reference buffer 146 and having to reserve space for separate reference electrode wells 140. The well design shown in FIG. 4C can also do away with the connecting conduits 144.

Figure 5A:
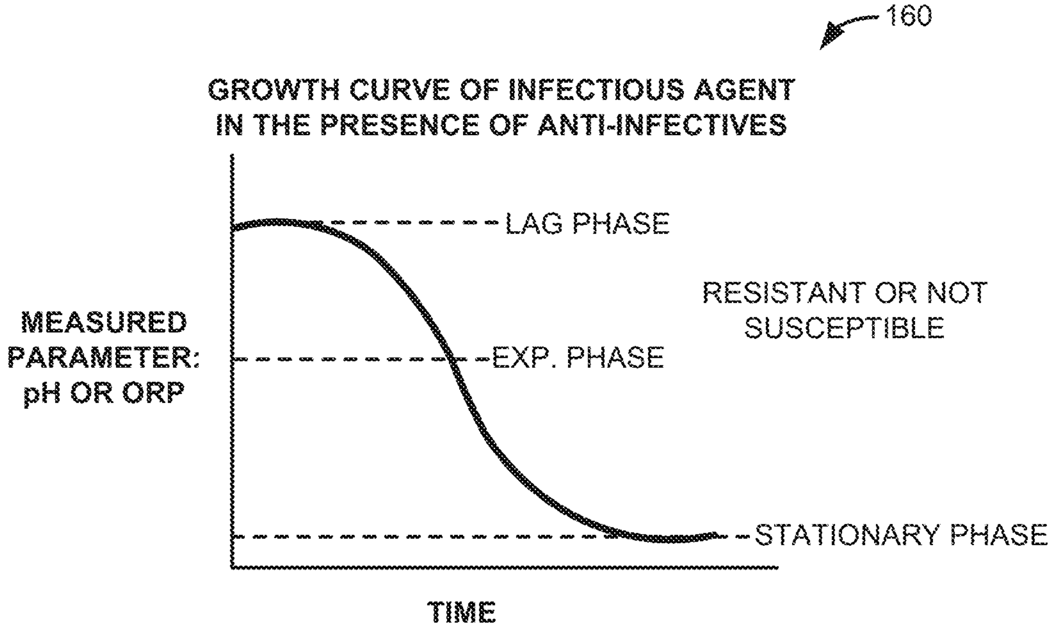
FIG. 5A illustrates an example growth curve of an infectious agent resistant to one or more anti-infectives.

FIG. 5A illustrates an example infectious agent growth curve 160 of an infectious agent 106 resistant or not susceptible to an anti-infective 108. The infectious agent growth curve 160 can be generated based on a change in the solution characteristic of the monitored inoculum solution 110. For example, the solution characteristic can be a change in the pH or ORP of the inoculum solution 110. The solution characteristic can be measured by the parameter analyzer 156 coupled to one or more active electrodes (e.g., the pH electrodes 130, the ORP electrodes 132, or a combination thereof) and the reference electrodes 142. More specifically, the parameter analyzer 156 can determine a potential difference between the active electrodes and the reference electrodes 142.

As shown in FIG. 5A, the pH or ORP (ΔV) of the inoculum solution 110 can change over time due to the energy use, oxygen uptake or release, or metabolism of the infectious agent 106 in solution. For example, the change in the solution characteristic can follow a sigmoidal pattern or shape or a step function or shape. The infectious agent growth curve 160 shown in FIG. 5A follows the classical growth curve pattern of a lag phase at the outset, followed by an exponential phase, and ending in a stationary phase. This shape or curve pattern can be attributed to cellular activity undertaken by the infectious agent 106 in solution. Moreover, this shape or curve pattern can also be attributed to a change in the amount of energy carriers (such as nicotinamide adenine dinucleotide (NADH) and flavin adenine dinucleotide ($FADH_2$)) in solution due to the growth of resistant infectious agent 106. Also, the shape of the curve shown in FIG. 5A can also be attributed to the amount of oxygen depleted in the inoculum solution 110 as a result of the growth of the infectious agent 106 in solution.

Figure 5B:
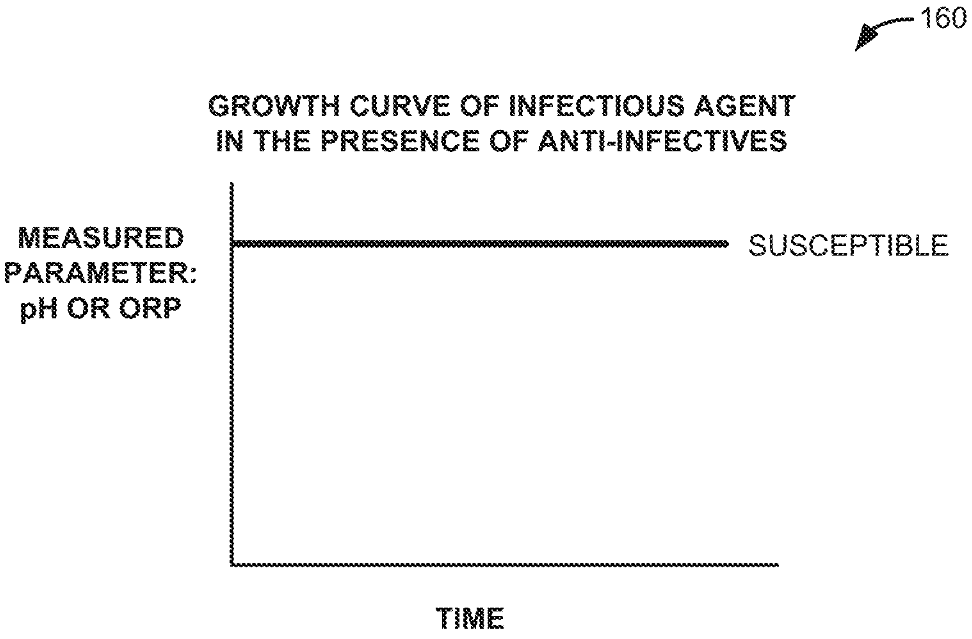
FIG. 5B illustrates an example growth curve of an infectious agent susceptible to one or more anti-infectives.

FIG. 5B illustrates an example infectious agent growth curve 160 of an infectious agent 106 susceptible or not resistant to an anti-infective 108. As shown in FIG. 5B, this infectious agent growth curve 160 can be relatively constant (e.g., a substantially flat line) over time. For example, the pH or ORP of the inoculum solution 110 can stay relatively constant or only exhibit changes within a predetermined threshold range due to the inhibitive effects of the anti-infective 108 on the infectious agent 106 in solution.

Figure 6:
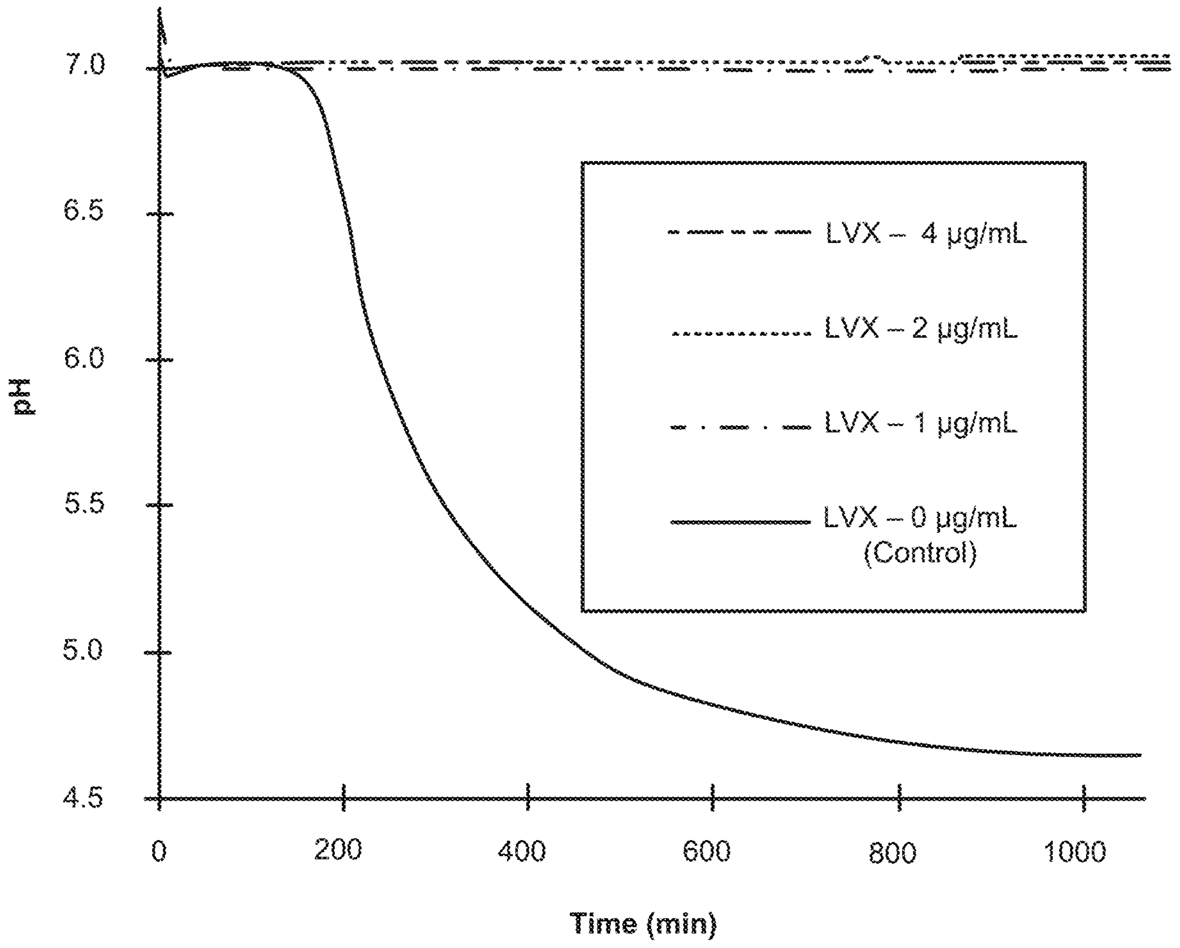
FIG. 6 illustrates a pH growth curve of bacteria in the presence of the antibiotic Levofloxacin.

FIG. 6 illustrates pH growth curves of *E. coli* in the presence of various concentrations of the antibiotic Levofloxacin. The growth curves were generated using a computing device 158 coupled to a parameter analyzer 156 coupled to the diagnostic device 102. Similar types of growth curves can also be generated using the computing device 158 coupled to the parameter analyzer 156 coupled to the diagnostic device 202.

An inoculum solution 110 comprising *E. coli* of an unknown strain (diluted in Mueller Hinton (MH) broth) was introduced to the sample receiving space 112 of the diagnostic device 102. The inoculum solution 110 was allowed to fill the plurality wells 120 of the diagnostic device 102 including the growth control wells 134 and a number of active electrode wells 136. A water immiscible liquid 152 was then introduced into the sample receiving space 112 to seal the wells 120 and the entire diagnostic device 102 was incubated at an elevated temperature.

The computing device 158 generated the growth curves based on a change in the pH of the inoculum solution 110 within a growth control well 134 and three active electrode wells 136. The growth control well 134 comprised a pH electrode 130 within the well and was devoid of the antibiotic. The active electrode wells 136 comprised dried Levofloxacin at concentrations of 1 μg/mL, 2 μg/mL, and 4 μg/mL.

The growth curve generated from measurements of the inoculum solution 110 within the growth control well 134 followed the classical growth pattern of bacteria having a lag phase at the outset, followed by an exponential phase, and ending in a stationary phase. This curve pattern or shape can be attributed to cellular activity undertaken by the active *E. coli* within the growth control well 134.

As shown in FIG. 6, the three growth curves generated from measurements of the inoculum solution 110 within the active electrode wells 136 were substantially flat lines showing relatively little change over the measurement period. This shows that *E. coli* within these three active electrode wells 136 succumbed to the inhibitive effectives of the Levofloxacin (i.e., no noticeable growth of the *E. coli* within the inoculum solution 110). As the minimum inhibitory concentration (MIC) of the Levofloxacin was 1 μg/mL, this strain of *E. coli* within the inoculum solution 110 was considered susceptible or non-resistant to Levofloxacin.

Figure 7A:
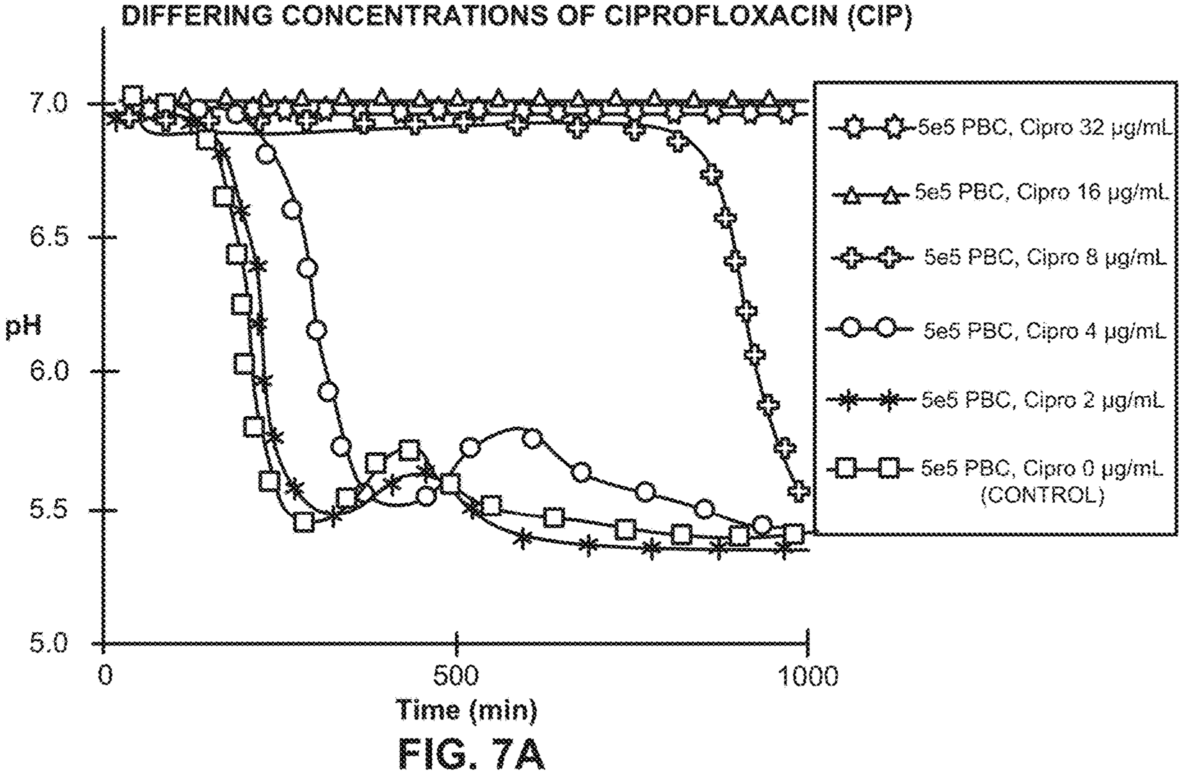
FIGS. 7A and 7B illustrate pH and ORP growth curves of bacteria in the presence of the antibiotic Ciprofloxacin, respectively.
Figure 7B:
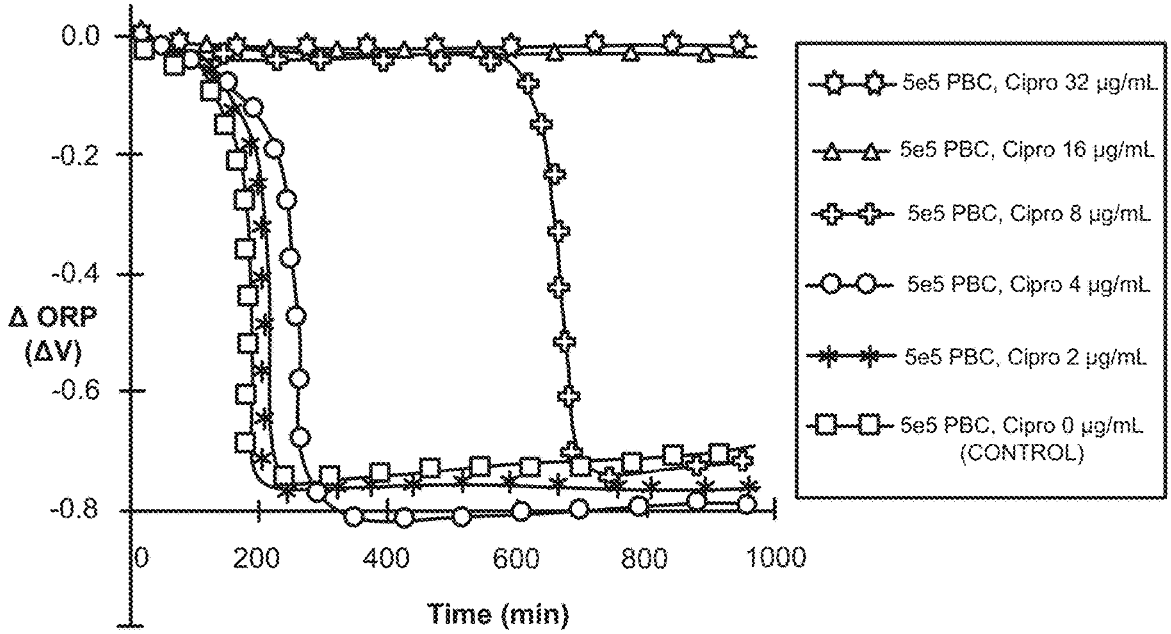

FIGS. 7A and 7B illustrate pH growth curves and ORP growth curves of *E. coli* in the presence of various concentrations of the antibiotic Ciprofloxacin, respectively. The growth curves were generated using a computing device 158 coupled to a parameter analyzer 156 coupled to the diagnostic device 102. Similar types of growth curves can also be generated using the computing device 158 coupled to the parameter analyzer 156 coupled to the diagnostic device 202.

An inoculum solution 110 comprising *E. coli* of an unknown strain (e.g., a positive blood culture (PBC) diluted to $5\times10^5$ colony-forming units (CFU)/mL of *E. coli* in Mueller Hinton (MH) broth) was introduced to the sample receiving space 112 of the diagnostic device 102. The inoculum solution 110 was allowed to fill the plurality wells 120 of the diagnostic device 102 including the growth control wells 134 and a number of active electrode wells 136. A water immiscible liquid 152 was then introduced into the sample receiving space 112 to seal the wells 120 and the entire diagnostic device 102 was incubated at an elevated temperature.

The computing device 158 generated the growth curves based on changes in the solution characteristics (e.g., changes in pH of the pH electrode wells 126 and changes in ORP of the ORP electrode wells 128) of the inoculum solution 110 within the growth control wells 134 and the various active electrode wells 136. The growth control wells 134 comprised at least one pH electrode well 126 and at least one ORP electrode well 128 devoid of the antibiotic. The active electrode wells 136 comprised dried Ciprofloxacin at concentrations of 2 μg/mL, 4 μg/mL, 8 μg/mL, 16 μg/mL, and 32 μg/mL.

As shown in FIGS. 7A and 7B, the growth curves generated from measurements of the inoculum solution 110 within the growth control wells 134 (e.g., the Cipro 0 μg/mL curves) followed the classical growth pattern of bacteria having a lag phase at the outset, followed by an exponential phase, and ending in a stationary phase. This curve pattern or shape can be attributed to cellular activity undertaken by the active *E. coli* within the growth control wells 134. FIGS. 7A and 7B also illustrate that the three growth curves generated from measurements of the inoculum solution 110 within the active electrode wells 136 comprising 2 μg/mL and 4 μg/mL of Ciprofloxacin mimicked and followed the growth pattern of the inoculum solution 110 within the growth control wells 134. This shows that this particular strain of *E. coli* within the inoculum solution 110 was resistant or not susceptible to Ciprofloxacin at such concentrations. However, the growth curve generated from measurements of the inoculum solution 110 within the active electrode well 136 comprising Ciprofloxacin at a concentration of 8 μg/mL exhibited a delayed change in pH and ORP. This can indicate a partial elimination of the bacteria (and a time-shifted re-growth of the bacteria) and evidence an intermediate susceptibility to the Ciprofloxacin at a concentration of 8 μg/mL.

Moreover, FIGS. 7A and 7B also show that the remaining two growth curves generated from measurements of the inoculum solution 110 within the active electrode wells 136 comprising Ciprofloxacin at concentrations of 16 μg/mL and 32 μg/mL were substantially flat lines showing relatively little change over the measurement period. This shows that *E. coli* within these active electrode wells 136 succumbed to the inhibitive effectives of the Ciprofloxacin (i.e., no noticeable growth of the *E. coli* within the inoculum solution 110) at such concentrations. Based on these results, the minimum inhibitory concentration (MIC) of Ciprofloxacin was determined to be approximately 16 μg/mL and this particular strain of *E. coli* within the inoculum solution 110 can be considered generally resistant to Ciprofloxacin.

It is contemplated by this disclosure that additional comparisons of the infectious agent growth curves can be made based on at least one of a (1) time to a pH threshold, (2) a length of an initial lag time, (3) a slope of an exponential phase of the growth curve, (4) a time to a stationary phase of the growth curve, (5) a total curve amplitude, and (6) an area under the curve to better fine-tune the MIC determination.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. For example, the flowcharts or process flows depicted in the figures do not require the particular order shown to achieve the desired result. Moreover, additional steps or operations may be provided or steps or operations may be eliminated to achieve the desired result.

It will be understood by one of ordinary skill in the art that all or a portion of the methods disclosed herein may be embodied in a non-transitory machine readable or accessible medium comprising instructions readable or executable by a processor or processing unit of a computing device or other type of machine.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure. The scope of the present invention is limited only by the appended claims.

What is claimed is:

1. A method of determining a susceptibility of an infectious agent to an anti-infective, the method comprising:

introducing an inoculum solution comprising the infectious agent into a sample receiving space, wherein the sample receiving space comprises a plurality of wells, wherein each of the wells comprises an oxidation reduction potential (ORP) electrode and a reference electrode, wherein at least one of the wells is a growth control well devoid of any anti-infective, and wherein at least two of the wells are active wells comprising the anti-infective at differing concentrations;

incubating the inoculum solution within the wells for a predetermined time period;

monitoring a solution characteristic of the inoculum solution within the active wells and the growth control well over the predetermined time period; and comparing the solution characteristic of the inoculum solution within the growth control well with the solution characteristic of the inoculum solution within the active wells to determine a minimum inhibitory concentration (MIC) of the anti-infective on the infectious agent.

2. The method of claim 1, wherein the solution characteristic of the inoculum solution is ORP and the MIC of the anti-infective on the infectious agent is determined by comparing the ORP of the inoculum solution within the growth control well with the ORP of the inoculum solution within the active wells.

3. The method of claim 1, wherein the active wells comprise at least a first ORP well and a second ORP well, wherein the first ORP well comprises the anti-infective at a first concentration; wherein the second ORP well comprises the anti-infective at a second concentration.

4. The method of claim 3, wherein the first concentration of the anti-infective is double the second concentration.

5. The method of claim 1, wherein the active wells comprise the anti-infective in at least one of a dried form and a lyophilized form.

6. The method of claim 1, wherein the active wells and the growth control well comprise a nutrient solution.

7. The method of claim 1, wherein the ORP electrode comprises a redox sensitive material.

8. The method of claim 7, wherein the redox sensitive material comprises at least one of silicon dioxide ($SiO_2$), aluminum oxide ($Al_2O_3$), titanium dioxide ($TiO_2$), tantalum pentoxide ($Ta_2O_5$), hafnium dioxide ($HfO_2$), iridium dioxide ($IrO_2$), ruthenium dioxide ($RuO_2$), zirconium dioxide ($ZrO_2$), or a combination thereof.

9. The method of claim 1, wherein the reference electrode is made in part of silver/silver chloride (Ag/AgCl), platinum, gold, or stainless steel.

10. The method of claim 1, wherein each of the wells has a well diameter and a well depth, and wherein an aspect ratio of the well depth to the well diameter is between about 1:1 to about 1:2.

11. A system to determine a susceptibility of an infectious agent to an anti-infective, the system comprising:

a sample receiving space configured to receive an inoculum solution,
  - wherein the sample receiving space comprises a plurality of wells,
  - wherein each of the wells comprises an oxidation reduction potential (ORP) electrode and a reference electrode,
  - wherein at least one of the wells is a growth control well devoid of any anti-infective, and
  - wherein at least two of the wells are active wells comprising the anti-infective at differing concentrations; and a parameter analyzer or computing device configured to:
  - monitor a solution characteristic of the inoculum solution within the active wells and the growth control well over a predetermined time period, and
  - compare the solution characteristic of the inoculum solution within the growth control well with the solution characteristic of the inoculum solution within the active wells to determine a minimum inhibitory concentration (MIC) of the anti-infective on the infectious agent.

12. The system of claim 11, wherein the solution characteristic of the inoculum solution is ORP and the MIC of the anti-infective on the infectious agent is determined by comparing the ORP of the inoculum solution within the growth control well with the ORP of the inoculum solution within the active wells.

13. The system of claim 11, wherein the active wells comprise at least a first ORP well and a second ORP well, wherein the first ORP well comprises the anti-infective at a first concentration; wherein the second ORP well comprises the anti-infective at a second concentration.

14. The system of claim 13, wherein the first concentration of the anti-infective is double the second concentration.

15. The system of claim 11, wherein the active wells comprise the anti-infective in at least one of a dried form and a lyophilized form.

16. The system of claim 11, wherein the active wells and the growth control well comprise a nutrient solution.

17. The system of claim 11, wherein the ORP electrode comprises a redox sensitive material.

18. The system of claim 17, wherein the redox sensitive material comprises at least one of silicon dioxide ($SiO_2$), aluminum oxide ($Al_2O_3$), titanium dioxide ($TiO_2$), tantalum pentoxide ($Ta_2O_5$), hafnium dioxide ($HfO_2$), iridium dioxide ($IrO_2$), ruthenium dioxide ($RuO_2$), zirconium dioxide ($ZrO_2$), or a combination thereof.

19. The system of claim 11, wherein the reference electrode is made in part of silver/silver chloride (Ag/AgCl), platinum, gold, or stainless steel.

20. The system of claim 11, wherein each of the wells has a well diameter and a well depth, and wherein an aspect ratio of the well depth to the well diameter is between about 1:1 to about 1:2.

* * * * *